United States Patent
Kuo et al.

(10) Patent No.: US 10,271,923 B2
(45) Date of Patent: Apr. 30, 2019

(54) REINFORCED ALIGNER HOOKS

(71) Applicant: Align Technology, Inc., San Jose, CA (US)

(72) Inventors: Eric Kuo, San Jose, CA (US); Artem Borovinskih, Union City, CA (US); Shiva Sambu, Santa Clara, CA (US)

(73) Assignee: Align Technology, Inc., San Jose, CA (US)

( * ) Notice: Subject to any disclaimer, the term of this patent is extended or adjusted under 35 U.S.C. 154(b) by 471 days.

(21) Appl. No.: 14/951,245

(22) Filed: Nov. 24, 2015

(65) Prior Publication Data
US 2016/0074137 A1     Mar. 17, 2016

Related U.S. Application Data

(62) Division of application No. 12/772,130, filed on Apr. 30, 2010, now abandoned.

(51) Int. Cl.
*A61C 7/08*     (2006.01)
*A61C 7/00*     (2006.01)
(Continued)

(52) U.S. Cl.
CPC ................ *A61C 7/002* (2013.01); *A61C 7/08* (2013.01); *B33Y 50/02* (2014.12); *G06F 17/5009* (2013.01); *A61C 9/0046* (2013.01)

(58) Field of Classification Search
CPC .................................. A61C 7/002; A61C 7/08
See application file for complete search history.

(56) References Cited

U.S. PATENT DOCUMENTS 2,467,432 A    4/1949   Kesling
3,407,500 A   10/1968   Kesling
(Continued)

FOREIGN PATENT DOCUMENTS

AU     3031677 A    5/1979
AU      517102 B2    7/1981
(Continued)

OTHER PUBLICATIONS

AADR. American Association for Dental Research, Summary of Activities, Mar. 20-23, 1980, Los ngeles, CA, p. 195.
(Continued)

*Primary Examiner* — Ralph Lewis
(74) *Attorney, Agent, or Firm* — Wilson Sonsini Goodrich & Rosati

(57) ABSTRACT

Orthodontic positioning devices, and related methods and systems, are disclosed for use with one or more orthodontic elastic members. The disclosed devices are configured to couple with an orthodontic elastic member so as to react a force from the elastic member into the appliance to, for example, generate traction forces on the patient's teeth to produce a desired occlusion. A positioning device includes a patient removable tooth positioning appliance having teeth receiving cavities shaped to receive and apply a resilient positioning force to a patient's teeth. The appliance includes a hook configured to interface with an orthodontic elastic member. The hook can be configured to be offset from a surface of a tooth when the appliance is coupled with the patient's teeth and no elastic member is coupled with the tooth. The hook can be curved so that the hook is more retentive on the aligner. The hook can be reinforced so that the reinforcement resists deformation when the elastic is in place.

20 Claims, 12 Drawing Sheets

(51) Int. Cl.
  *B33Y 50/02* (2015.01)
  *G06F 17/50* (2006.01)
  *A61C 9/00* (2006.01)

(56) References Cited

U.S. PATENT DOCUMENTS

| | | |
|---|---|---|
| 3,600,808 A | 8/1971 | Reeve |
| 3,660,900 A | 5/1972 | Andrews |
| 3,683,502 A | 8/1972 | Wallshein |
| 3,738,005 A | 6/1973 | Cohen |
| 3,860,803 A | 1/1975 | Levine |
| 3,916,526 A | 11/1975 | Schudy |
| 3,922,786 A | 12/1975 | Lavin |
| 3,950,851 A | 4/1976 | Bergersen |
| 3,983,628 A | 10/1976 | Acevedo |
| 4,014,096 A | 3/1977 | Dellinger |
| 4,195,046 A | 3/1980 | Kesling |
| 4,253,828 A | 3/1981 | Coles et al. |
| 4,324,546 A | 4/1982 | Heitlinger et al. |
| 4,324,547 A | 4/1982 | Arcan et al. |
| 4,348,178 A | 9/1982 | Kurz |
| 4,478,580 A | 10/1984 | Barrut |
| 4,500,294 A | 2/1985 | Lewis |
| 4,504,225 A | 3/1985 | Yoshii |
| 4,505,673 A | 3/1985 | Yoshii |
| 4,526,540 A | 7/1985 | Dellinger |
| 4,575,330 A | 3/1986 | Hull |
| 4,575,805 A | 3/1986 | Moermann et al. |
| 4,591,341 A | 5/1986 | Andrews |
| 4,609,349 A | 9/1986 | Cain |
| 4,611,288 A | 9/1986 | Duret et al. |
| 4,656,860 A | 4/1987 | Orthuber et al. |
| 4,663,720 A | 5/1987 | Duret et al. |
| 4,664,626 A | 5/1987 | Kesling |
| 4,676,747 A | 6/1987 | Kesling |
| 4,742,464 A | 5/1988 | Duret et al. |
| 4,755,139 A | 7/1988 | Abbatte et al. |
| 4,763,791 A | 8/1988 | Halverson et al. |
| 4,793,803 A | 12/1988 | Martz |
| 4,798,534 A | 1/1989 | Breads |
| 4,836,778 A | 6/1989 | Baumrind et al. |
| 4,837,732 A | 6/1989 | Brandestini et al. |
| 4,850,864 A | 7/1989 | Diamond |
| 4,850,865 A | 7/1989 | Napolitano |
| 4,856,991 A | 8/1989 | Breads et al. |
| 4,877,398 A | 10/1989 | Kesling |
| 4,880,380 A | 11/1989 | Martz |
| 4,889,238 A | 12/1989 | Batchelor |
| 4,890,608 A | 1/1990 | Steer |
| 4,935,635 A | 6/1990 | O'Harra |
| 4,936,862 A | 6/1990 | Walker et al. |
| 4,937,928 A | 7/1990 | van der Zel |
| 4,941,826 A | 7/1990 | Loran et al. |
| 4,964,770 A | 10/1990 | Steinbichler et al. |
| 4,975,052 A | 12/1990 | Spencer et al. |
| 4,983,334 A | 1/1991 | Adell |
| 5,011,405 A | 4/1991 | Lemchen |
| 5,017,133 A | 5/1991 | Miura |
| 5,027,281 A | 6/1991 | Rekow et al. |
| 5,035,613 A | 7/1991 | Breads et al. |
| 5,055,039 A | 10/1991 | Abbatte et al. |
| 5,059,118 A | 10/1991 | Breads et al. |
| 5,087,202 A | 2/1992 | Krenkel |
| 5,100,316 A | 3/1992 | Wildman |
| 5,121,333 A | 6/1992 | Riley et al. |
| 5,125,832 A | 6/1992 | Kesling |
| 5,128,870 A | 7/1992 | Erdman et al. |
| 5,130,064 A | 7/1992 | Smalley |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,176,517 A | 1/1993 | Truax |
| 5,184,306 A | 2/1993 | Erdman et al. |
| 5,186,623 A | 2/1993 | Breads et al. |
| 5,257,203 A | 10/1993 | Riley et al. |
| 5,273,429 A | 12/1993 | Rekow et al. |
| 5,278,756 A | 1/1994 | Lemchen et al. |
| 5,328,362 A | 7/1994 | Watson et al. |
| 5,338,198 A | 8/1994 | Wu et al. |
| 5,340,309 A | 8/1994 | Robertson |
| 5,342,202 A | 8/1994 | Deshayes |
| 5,368,478 A | 11/1994 | Andreiko et al. |
| 5,382,164 A | 1/1995 | Stern |
| 5,395,238 A | 3/1995 | Andreiko et al. |
| 5,440,326 A | 8/1995 | Quinn |
| 5,440,496 A | 8/1995 | Andersson et al. |
| 5,447,432 A | 9/1995 | Andreiko et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,431,562 A | 11/1995 | Andreiko et al. |
| 5,474,448 A | 12/1995 | Andreiko et al. |
| RE35,169 E | 3/1996 | Lemchen et al. |
| 5,518,397 A | 5/1996 | Andreiko et al. |
| 5,528,735 A | 6/1996 | Strasnick et al. |
| 5,533,895 A | 7/1996 | Andreiko et al. |
| 5,542,842 A | 8/1996 | Andreiko et al. |
| 5,549,476 A | 8/1996 | Stern |
| 5,562,448 A | 10/1996 | Mushabac |
| 5,587,912 A | 12/1996 | Andersson et al. |
| 5,605,459 A | 2/1997 | Kuroda et al. |
| 5,607,305 A | 3/1997 | Andersson et al. |
| 5,614,075 A | 3/1997 | Andre |
| 5,621,648 A | 4/1997 | Crump |
| 5,645,420 A | 7/1997 | Bergersen |
| 5,645,421 A | 7/1997 | Slootsky |
| 5,655,653 A | 8/1997 | Chester |
| 5,683,243 A | 11/1997 | Andreiko et al. |
| 5,692,894 A | 12/1997 | Schwartz et al. |
| 5,725,376 A | 3/1998 | Poirier |
| 5,725,378 A | 3/1998 | Wang |
| 5,733,126 A | 3/1998 | Andersson et al. |
| 5,740,267 A | 4/1998 | Echerer et al. |
| 5,742,700 A | 4/1998 | Yoon et al. |
| 5,799,100 A | 8/1998 | Clarke et al. |
| 5,800,174 A | 9/1998 | Andersson |
| 5,823,778 A | 10/1998 | Schmitt et al. |
| 5,848,115 A | 12/1998 | Little et al. |
| 5,857,853 A | 1/1999 | van Nifterick et al. |
| 5,866,058 A | 2/1999 | Batchelder et al. |
| 5,879,158 A | 3/1999 | Doyle et al. |
| 5,880,961 A | 3/1999 | Crump |
| 5,880,962 A | 3/1999 | Andersson et al. |
| 5,934,288 A | 8/1999 | Avila et al. |
| 5,957,686 A | 9/1999 | Anthony |
| 5,964,587 A | 10/1999 | Sato |
| 5,971,754 A | 10/1999 | Sondhi et al. |
| 5,975,893 A * | 11/1999 | Chishti ............... A61C 7/00 433/6 |
| 6,015,289 A | 1/2000 | Andreiko et al. |
| 6,044,309 A | 3/2000 | Honda |
| 6,049,743 A | 4/2000 | Baba |
| 6,062,861 A | 5/2000 | Andersson |
| 6,068,482 A | 5/2000 | Snow |
| 6,099,314 A | 8/2000 | Kopelman et al. |
| 6,123,544 A | 9/2000 | Cleary |
| 6,152,731 A | 11/2000 | Jordon et al. |
| 6,183,248 B1 | 2/2001 | Chishti et al. |
| 6,190,165 B1 | 2/2001 | Andreiko et al. |
| 6,217,325 B1 | 4/2001 | Chishti et al. |
| 6,217,334 B1 | 4/2001 | Hultgren |
| 6,244,861 B1 | 6/2001 | Andreiko et al. |
| 6,309,215 B1 | 10/2001 | Phan et al. |
| 6,315,553 B1 | 11/2001 | Sachdeva et al. |
| 6,322,359 B1 | 11/2001 | Jordan et al. |
| 6,350,120 B1 | 2/2002 | Sachdeva |
| 6,382,975 B1 | 5/2002 | Poirier |
| 6,398,548 B1 | 6/2002 | Muhammad et al. |
| 6,402,707 B1 | 6/2002 | Ernst |
| 6,482,298 B1 | 11/2002 | Bhatnagar |
| 6,524,101 B1 | 2/2003 | Phan et al. |
| 6,554,611 B2 | 4/2003 | Chishti et al. |

(56) References Cited

U.S. PATENT DOCUMENTS

| | | | |
|---|---|---|---|
| 6,572,372 B1* | 6/2003 | Phan | A61C 7/00 433/18 |
| 6,604,527 B1 | 8/2003 | Palmisano | |
| 6,629,840 B2 | 10/2003 | Chishti et al. | |
| 6,705,863 B2 | 3/2004 | Phan et al. | |
| 6,722,880 B2 | 4/2004 | Chishti et al. | |
| 7,077,646 B2* | 7/2006 | Hilliard | A61C 7/00 433/18 |
| 7,125,248 B2* | 10/2006 | Phan | A61C 7/00 433/6 |
| 7,267,545 B2* | 9/2007 | Oda | A61C 7/287 433/10 |
| 7,771,195 B2* | 8/2010 | Knopp | A61C 7/00 433/24 |
| 8,060,236 B2* | 11/2011 | Hilliard | A61C 7/08 433/218 |
| 2002/0006597 A1 | 1/2002 | Andreiko et al. | |
| 2002/0177108 A1 | 11/2002 | Pavlovskaia et al. | |
| 2003/0009252 A1 | 1/2003 | Pavlovskaia et al. | |
| 2003/0139834 A1 | 7/2003 | Nikolskiy et al. | |
| 2003/0224311 A1 | 12/2003 | Cronauer | |
| 2004/0128010 A1 | 7/2004 | Pavlovskaia et al. | |
| 2005/0055118 A1 | 3/2005 | Nikolskiy et al. | |
| 2006/0008760 A1* | 1/2006 | Phan | A61C 7/00 433/6 |
| 2006/0188834 A1 | 8/2006 | Hilliard | |
| 2007/0231765 A1 | 10/2007 | Phan | |
| 2007/0283967 A1 | 12/2007 | Bailey | |
| 2008/0020337 A1* | 1/2008 | Phan | A61C 7/00 433/6 |
| 2008/0254402 A1 | 10/2008 | Hilliard | |
| 2011/0269092 A1 | 11/2011 | Kuo et al. | |

FOREIGN PATENT DOCUMENTS

| | | |
|---|---|---|
| AU | 5598894 A | 6/1994 |
| CA | 1121955 | 4/1982 |
| DE | 2749802 | 5/1978 |
| DE | 69327661 T | 7/2000 |
| EP | 0091876 A1 | 10/1983 |
| EP | 0299490 A2 | 1/1989 |
| EP | 0376873 A2 | 7/1990 |
| EP | 0490848 A2 | 6/1992 |
| EP | 0541500 A1 | 5/1993 |
| EP | 0667753 B1 | 8/1995 |
| EP | 0731673 B1 | 9/1996 |
| EP | 0774933 B1 | 5/1997 |
| ES | 463897 | 1/1980 |
| FR | 2369828 A1 | 6/1978 |
| FR | 2652256 A1 | 3/1991 |
| GB | 15500777 | 8/1979 |
| JP | 53-058191 | 5/1978 |
| JP | 04-028359 | 1/1992 |
| JP | 08-508174 | 9/1996 |
| WO | WO 90/08512 A1 | 8/1990 |
| WO | WO 91/04713 A1 | 4/1991 |
| WO | WO 94/10935 A1 | 5/1994 |
| WO | WO 98/32394 A1 | 7/1998 |
| WO | WO 98/44865 A1 | 10/1998 |
| WO | WO 98/58596 A1 | 12/1998 |
| WO | WO 2006/118771 A2 | 11/2006 |

OTHER PUBLICATIONS

Alcaniz, et aL, "An Advanced System for the Simulation and Planning of Orthodontic Treatments," Karl Heinz Hohne and Ron Kikinis (eds.), Visualization in Biomedical Computing, 4th Intl. Conf., VBC '96, Hamburg, Germany, Sep. 22-25, 1996, Springer-Verlag, pp. 511-520.

Alexander et al., "The DigiGraph Work Station Part 2 Clinical Management," JCO, pp. 402-407 (Jul. 1990).

Altschuler et al., "Analysis of 3-D Data for Comparative 3-D Serial Growth Pattern Studies of Oral-Facial Structures," AADR Abstracts, Program and Abstracts of Papers, 57th General Session, IADR Annual Session, Mar. 29, 1979-Apr. 1, 1979, New Orleans Marriot, Journal of Dental Research, vol. 58, Jan. 1979, Special Issue A, p. 221.

Altschuler et al., "Laser Electro-Optic System for Rapid Three-Dimensional (3D) Topographic Mapping of Surfaces," Optical Engineering, 20(6):953-961 (1981).

Altschuler et al., "Measuring Surfaces Space-Coded by a Laser-Projected Dot Matrix," SPIE Imaging q Applications for Automated Industrial Inspection and Assembly, vol. 182, p. 187-191 (1979).

Altschuler, "3D Mapping of Maxillo-Facial Prosthesis," AADR Abstract #607, 2 pages total, (1980).

Andersson et al., "Clinical Results with Titanium Crowns Fabricated with Machine Duplication and Spark Erosion," Acta. Odontol. Scand., 47:279-286 (1989).

Andrews, The Six Keys to Optimal Occlusion Straight Wire, Chapter 3, pp. 13-24 (1989).

Bartels, et al., An Introduction to Splines for Use in Computer Graphics and Geometric Modeling, Morgan Kaufmann Publishers, pp. 422-425 (1987).

Baumrind et al., "A Stereophotogrammetric System for the Detection of Prosthesis Loosening in Total Hip Arthroplasty," NATO Symposium on Applications of Human Biostereometrics, Jul. 9-13, 1978, SPIE, vol. 166, pp. 112-123.

Baumrind et al., "Mapping the Skull in 3-D," reprinted from J. Calif. Dent. Assoc., 48(2), 11 pages total, (1972 Fall Issue).

Baumrind, "A System for Craniofacial Mapping Through the Integration of Data from Stereo X-Ray Films and Stereo Photographs," an invited paper submitted to the 1975 American Society of Photogram Symposium on Close-Range Photogram Systems, University of Ill., Aug. 26-30, 1975, pp. 142-166.

Baumrind, "Integrated Three-Dimensional Craniofacial Mapping: Background, Principles, and Perspectives," Semin. in Orthod., 7(4):223-232 (Dec. 2001).

Begole et al., "A Computer System for the Analysis of Dental Casts," The Angle Orthod., 51(3):253-259 (Jul. 1981).

Bernard et al.,"Computerized Diagnosis in Orthodontics for Epidemiological Studies: A ProgressReport," Abstract, J. Dental Res. Special Issue, vol. 67, p. 169, paper presented at International Association for Dental Research 66th General Session, Mar. 9-13, 1988, Montreal, Canada.

Bhatia et al., "A Computer-Aided Design for Orthognathic Surgery," Br. J. Oral Maxillofac. Surg., 22:237-253 (1984).

Biggerstaff et al., "Computerized Analysis of Occlusion in the Postcanine Dentition," Am. J. Orthod., 61(3): 245-254 (Mar. 1972).

Biggerstaff, "Computerized Diagnostic Setups and Simulations," Angle Orthod., 40(1):28-36 (Jan. 1970).

Biostar Operation & Training Manual. Great Lakes Orthodontics, Ltd. 199 Fire Tower Drive, Tonawanda, New York. 14150-5890, 20 pages total (1990).

Blu, et al., "Linear interpolation revitalized", IEEE Trans. Image Proc., 13(5):710-719 (May 2004).

Bourke, "Coordinate System Transformation," (Jun. 1996), p. 1, retrieved from the Internet Nov. 5, 2004, URL <http://astronomy.swin.edu.au/—pbourke/prolection/coords>.

Boyd et al., "Three Dimensional Diagnosis and Orthodontic Treatment of Complex Malocclusions With the Invisalipn Appliance," Semin. Orthod., 7(4):274-293 (Dec. 2001).

Brandestini et al., "Computer Machined Ceramic Inlays: In Vitro Marginal Adaptation," J. Dent. Res. Special Issue, Abstract 305, vol. 64, p. 208 (1985).

Brook et al., "An Image Analysis System for the Determination of Tooth Dimensions from Study Casts: Comparison with Manual Measurements of Mesio-distal Diameter," J. Dent. Res., 65(3):428-431 (Mar. 1986).

Burstone (interview), "Dr. Charles J. Burstone on The Uses of the Computer in Orthodontic Practice (Part 1)," J. Clin. Orthod., 13(7):442-453 (Jul. 1979).

Burstone (interview), "Dr. Charles J. Burstone on The Uses of the Computer in Orthodontic Practice (Part 2)," J. Clin. Orthod., 13(8):539-551 (Aug. 1979).

(56) References Cited

OTHER PUBLICATIONS

Burstone et al., Precision Adjustment of the Transpalatal Lingual Arch: Computer Arch Form Predetermination, Am, Journal of Orthodontics, vol. 79, No. 2 (Feb. 1981), pp. 115-133.
Cardinal Industrial Finishes, Powder Coatings information posted at <http://www.cardinalpaint.com> on Aug. 25, 2000, 2 pages.
Carnaghan, "An Alternative to Holograms for the Portrayal of Human Teeth," 4th Int'l. Conf. on Holographic Systems, Components and Applications, Sep. 15, 1993, pp. 228-231.
Chaconas et al., "The DigiGraph Work Station, Part 1, Basic Concepts," JCO, pp. 360-367 (Jun. 1990).
Chafetz et al., "Subsidence of the Femoral Prosthesis, A Stereophotogrammetric Evaluation," Clin. Orthop. Relat. Res., No. 201, pp. 60-67 (Dec. 1985).
Chiappone, (1980). Constructing the Gnathologic Setup and Positioner, J. Clin. Orthod, vol. 14, pp. 121-133.
Cottingham, (1969). Gnathologic Clear Plastic Positioner, Am. J. Orthod, vol. 55, pp. 23-31.
Crawford, "CAD/CAM in the Dental Office: Does It Work?", Canadian Dental Journal, vol. 57, No. 2, pp. 121-123 (Feb. 1991).
Crawford, "Computers in Dentistry: Part 1: CAD/CAM: The Computer Moves Chairside," "Part 2: F. Duret—A Man With A Vision," "Part 3: The Computer Gives New Vision—Literally," "Part 4: Bytes 'N Bites" The Computer Moves From the Front Desk to the Operatory, Canadian Dental Journal, vol. 54(9), pp. 661-666 (1988).
Crooks, "CAD/CAM Comes to USC," USC Dentistry, pp. 14-17 (Spring 1990).
Cureton, Correcting Malaligned Mandibular Incisors with Removable Retainers, J. Clin. Orthod, vol. 30, No. 7 (1996) pp. 390-395.
Curry et al., "Integrated Three-Dimensional Craniofacial Mapping at the Craniofacial Research Instrumentation Laboratory/University of the Pacific," Semin. Orthod., 7(4):258-265 (Dec. 2001).
Cutting et al., "Three-Dimensional Computer-Assisted Design of Craniofacial Surgical Procedures: Optimization and Interaction with Cephalometric and CT-Based Models," Plast. 77(6):877-885 (Jun. 1986).
DCS Dental AG, "The CAD/CAM 'DCS Titan System' for Production of Crowns/Bridges," DSC Production, pp. 1-7 (Jan. 1992).
Definition for gingiva. Dictionary.com p. 1-3. Retrieved from the internet Nov. 5, 2004 <http://reference.com/search/search?q=gingiva>.
Defranco et al., "Three-Dimensional Large Displacement Analysis of Orthodontic Appliances," J. Biomechanics, 9:793-801 (1976).
Dental Institute University of Zurich Switzerland, Program for International Symposium on Computer Restorations: State of the Art of the CEREC-Method, May 1991, 2 pages total.
Dentrac Corporation, Dentrac document, pp. 4-13 (1992).
DENT-X posted on Sep. 24, 1998 at <http://www.dent-x.com/DentSim.htm>, 6 pages.
Doyle, "Digital Dentistry," Computer Graphics World, pp. 50-52, 54 (Oct. 2000).
DuraClearTM product information, Allesee Orthodontic Appliances—Pro Lab, 1 page (1997).
Duret et al, "CAD-CAM in Dentistry," J. Am. Dent. Assoc. 117:715-720 (Nov. 1988).
Duret et al., "CAD/CAM Imaging in Dentistry," Curr. Opin. Dent., 1:150-154 (1991).
Duret, "The Dental CAD/CAM, General Description of the Project," Hennson International Product Brochure, 18 pages total, Jan. 1986.
Duret,"Vers Une Prosthese Informatisee," (English translation attached), Tonus, vol. 75, pp. 55-57 (Nov. 15, 1985).
Economides, "The Microcomputer in the Orthodontic Office," JCO, pp. 767-772 (Nov. 1979).
Elsasser, Some Observations on the History and Uses of the Kesling Positioner, Am. J. Orthod. (1950) 36:368-374.
English translation of Japanese Laid-Open Publication No. 63-11148 to inventor T. Ozukuri (Laid-Open on Jan. 18, 1998) pp. 1-7.
Felton et al., "A Computerized Analysis of the Shape and Stability of Mandibular Arch Form," Am. J. Orthod. Dentofacial Orthop., 92(6):478-483 (Dec. 1987).
Friede et al., "Accuracy of Cephalometric Prediction in Orthognathic Surgery," Abstract of Papers, J. Dent. Res., 70:754-760 (1987).
Futterling et a/., "Automated Finite Element Modeling of a Human Mandible with Dental Implants," JS WSCG '98—Conference Program, retrieved from the Internet: <http://wscg.zcu.cz/wscg98/papers98/Strasser 98.pdf, 8 pages.
Gao et al., "3-D element Generation for Multi-Connected Complex Dental and Mandibular Structure," Proc. Intl Workshop on Medical Imaging and Augmented Reality, pp. 267-271 (Jun. 12, 2001).
Gim-Alldent Deutschland, "Das DUX System: Die Technik," 2 pages total (2002).
Gottleib et al., "JCO Interviews Dr. James A. McNamura, Jr., on the Frankel Appliance: Part 2: Clinical 1-1 Management," J. Clin. Orthod., 16(6):390-407 (Jun. 1982).
Grayson, "New Methods for Three Dimensional Analysis of Craniofacial Deformity, Symposium: Computerized Facial Imaging in Oral and Maxiiofacial Surgery," AAOMS, 3 pages total, (Sep. 13, 1990).
Guess et al., "Computer Treatment Estimates in Orthodontics and Orthognathic Surgery," JCO, pp. 262-28 (Apr. 1989).
Heaven et al. "Computer-Based Image Analysis of Artificial Root Surface Caries," Abstracts of Papers, J. Dent. Res., 70:528 (Apr. 17-21, 1991).
Highbeam Research, "Simulating Stress Put on Jaw," Tooling & Production [online], Nov. 1996, n pp. 1-2, retrieved from the Internet on Nov. 5, 2004, URL http://static.highbeam.com/t/toolingampproduction/november011996/simulatingstressputonfa . . . >.
Hikage, "Integrated Orthodontic Management System for Virtual Three-Dimensional Computer Graphic Simulation and Optical Video Image Database for Diagnosis and Treatment Planning", Journal of Japan KA Orthodontic Society, Feb. 1987, English translation, pp. 1-38, Japanese version, 46(2), pp. 248-269 (60 pages total).
Hoffmann, et al., "Role of Cephalometry for Planning of Jaw Orthopedics and Jaw Surgery Procedures," (Article Summary in English, article in German), Informatbnen, pp. 375-396 (Mar. 1991).
Hojjatie et al., "Three-Dimensional Finite Element Analysis of Glass-Ceramic Dental Crowns," J. Biomech., 23(11):1157-1166 (1990).
Huckins, "CAD-CAM Generated Mandibular Model Prototype from MRI Data," AAOMS, p. 96 (1999).
Important Tip About Wearing the Red White & Blue Active Clear Retainer System, Allesee Orthodontic Appliances—Pro Lab, 1 page 1998).
JCO Interviews, Craig Andreiko , DDS, MS on the Elan and Orthos Systems, JCO, pp. 459-468 (Aug. 1994).
JCO Interviews, Dr. Homer W. Phillips on Computers in Orthodontic Practice, Part 2, JCO. 1997; 1983:819-831.
Jerrold, "The Problem, Electronic Data Transmission and the Law," AJO-DO, pp. 478-479 (Apr. 1988).
Jones et al., "An Assessment of the Fit of a Parabolic Curve to Pre- and Post-Treatment Dental Arches," Br. J. Orthod., 16:85-93 (1989).
JP Faber et al., "Computerized Interactive Orthodontic Treatment Planning," Am. J. Orthod., 73(1):36-46 (Jan. 1978).
Kamada et.al., Case Reports on Tooth Positioners Using LTV Vinyl Silicone Rubber, J. Nihon University School of Dentistry (1984) 26(1): 11-29.
Kamada et.al., Construction of Tooth Positioners with LTV Vinyl Silicone Rubber and Some Case KJ Reports, J. Nihon University School of Dentistry (1982) 24(1):1-27.
Kanazawa et al., "Three-Dimensional Measurements of the Occlusal Surfaces of Upper Molars in a Dutch Population," J. Dent Res., 63(11):1298-1301 (Nov. 1984).
Kesling et al., The Philosophy of the Tooth Positioning Appliance, American Journal of Orthodontics and Oral surgery. 1945; 31:297-304.
Kesling, Coordinating the Predetermined Pattern and Tooth Positioner with Conventional Treatment, Am. J. Orthod. Oral Surg. (1946) 32:285-293.

(56) References Cited

OTHER PUBLICATIONS

Kleeman et al., The Speed Positioner, J. Clin. Orthod. (1996) 30:673-680.
Kochanek, "Interpolating Splines with Local Tension, Continuity and Bias Control," Computer Graphics, 18(3):33-41 (Jul. 1984).
Oral Surgery (1945) 31 :297-30.
Kunii et al., "Articulation Simulation for an Intelligent Dental Care System," Displays 15:181-188 (1994).
Kuroda et al., Three-Dimensional Dental Cast Analyzing System Using Laser Scanning, Am. J. Orthod. Dentofac. Orthop. (1996) 110:365-369.
Laurendeau, et al., "A Computer-Vision Technique for the Acquisition and Processing of 3-D Profiles of 7 Dental Imprints: An Application in Orthodontics," IEEE Transactions on Medical Imaging, 10(3):453-461 (Sep. 1991).
Leinfelder, et al., "A New Method for Generating Ceramic Restorations: a CAD-CAM System," J. Am. 1-1 Dent. Assoc., 118(6):703-707 (Jun. 1989).
Manetti, et al., "Computer-Aided Cefalometry and New Mechanics in Orthodontics," (Article Summary in English, article in German), Fortschr Kieferorthop. 44, 370-376 (Nr. 5), 1983.
McCann, "Inside the ADA," J. Amer. Dent. Assoc., 118:286-294 (Mar. 1989).
McNamara et al., "Invisible Retainers," J. Cfin. Orthod., pp. 570-578 (Aug. 1985).
McNamara et al., Orthodontic and Orthopedic Treatment in the Mixed Dentition, Needham Press, pp. 347-353 (Jan. 1993).
Moermann et al., "Computer Machined Adhesive Porcelain Inlays: Margin Adaptation after Fatigue Stress," IADR Abstract 339, J. Dent. Res., 66(a):763 (1987).
Moles, "Correcting Mild Malalignments—As Easy As One, Two, Three," AOA/Pro Corner, vol. 11, No. 1, 2 pages (2002).
Mormann et al., "Marginale Adaptation von adhasuven Porzellaninlays in vitro," Separatdruck aus:Schweiz. Mschr. Zahnmed. 95: 1118-1129, 1985.
Nahoum, "The Vacuum Formed Dental Contour Appliance," N. Y. State Dent. J., 30(9):385-390 (Nov. 1964).
Nash, "CEREC CAD/CAM Inlays: Aesthetics and Durability in a Single Appointment," Dent. Today, 9(8):20, 22-23 (Oct. 1990).
Nishiyama et al., "A New Construction of Tooth Repositioner by LTV Vinyl Silicone Rubber," J. Nihon Univ. Sch. Dent., 19(2):93-102 (1977).
Paul et al., "Digital Documentation of Individual Human Jaw and Tooth Forms for Applications in Orthodontics, Oral Surgery and Forensic Medicine" Proc. of the 24th Annual Conf. of the IEEE Industrial Electronics Society (IECON '98), Sep. 4, 1998, pp. 2415-2418.
Pinkham, "Foolish Concept Propels Technology," Dentist, 3 pages total, Jan./Feb. 1989.
Pinkham, "Inventor's CAD/CAM May Transform Dentistry," Dentist, 3 pages total, Sep. 1990.
Ponitz, "Invisible Retainers," Am. J. Orthod., 59(3):266-272 (Mar. 1971).
Procera Research Projects, "Procera Research Projects 1993—Abstract Collection," pp. 3-7 28 (1993).
Proffit et al., Contemporary Orthodontics, (Second Ed.), Chapter 15, Mosby Inc., pp. 470-533 (Oct. 1993).
Raintree Essix & ARS Materials, Inc., Raintree Essix, Technical Magazine Table of contents and Essix Appliances, <http://www.essix.com/magazine/defaulthtml> Aug. 13, 1997.
Redmond et al., "Clinical Implications of Digital Orthodontics," Am. J. Orthod. Dentofacial Orthop., 117(2):240-242 (2000).
Rekow et al. "CAD/CAM for Dental Restorations—Some of the Curious Challenges," IEEE Trans. Biomed. Eng., 38(4):314-318 (Apr. 1991).
Rekow et al., "Comparison of Three Data Acquisition Techniques for 3-D Tooth Surface Mapping," Annual International Conference of the IEEE Engineering in Medicine and Biology Society, 13(1):344-345 1991.
Rekow, "A Review of the Developments in Dental CAD/CAM Systems," (contains references to Japanese efforts and content of the papers of particular interest to the clinician are indicated with a one line summary of their content in the bibliography), Curr. Opin. Dent., 2:25-33 (Jun. 1992).
Rekow, "CAD/CAM in Dentistry: A Historical Perspective and View of the Future," J. Can. Dent. Assoc., 58(4):283, 287-288 (Apr. 1992).
Rekow, "Computer-Aided Design and Manufacturing in Dentistry: A Review of the State of the Art," J. Prosthet. Dent., 58(4):512-516 (Oct. 1987).
Rekow, "Dental CAD-CAM Systems: What is the State of the Art?", J. Amer. Dent. Assoc., 122:43-48 1991.
Rekow, "Feasibility of an Automated System for Production of Dental Restorations, Ph.D. Thesis," Univ. of Minnesota, 244 pages total, Nov. 1988.
Richmond et al., "The Development of a 3D Cast Analysis System," Br. J. Orthod., 13(1):53-54 (Jan. 1986).
Richmond et al., "The Development of the PAR Index (Peer Assessment Rating): Reliability and Validity," Eur. J. Orthod., 14:125-139 (1992).
Richmond, "Recording the Dental Cast in Three Dimensions," Am. J. Orthod. Dentofacial Orthop., 92(3):199-206 (Sep. 1987).
Rudge, "Dental Arch Analysis: Arch Form, A Review of the Literature," Eur. J. Orthod., 3(4):279-284 1981.
Sakuda et al., "Integrated Information-Processing System in Clinical Orthodontics: An Approach with Use of a Computer Network System," Am. J. Orthod. Dentofacial Orthop., 101(3): 210-220 (Mar. 1992).
Schellhas et al., "Three-Dimensional Computed Tomography in Maxillofacial Surgical Planning," Arch. Otolamp!. Head Neck Surg., 114:438-442 (Apr. 1988).
Schroeder et al., Eds. The Visual Toolkit, Prentice Hall PRT, New Jersey (1998) Chapters 6, 8 & 9, (pp. 153-210,309-354, and 355-428, respectively).
Shilliday, (1971). Minimizing finishing problems with the mini-positioner, Am. J. Orthod. 59:596-599.
Siemens, "CEREC—Computer-Reconstruction," High Tech in der Zahnmedizin, 14 pages total (2004).
Sinclair, "The Readers' Corner," J. Clin. Orthod., 26(6):369-372 (Jun. 1992).
Sirona Dental Systems GmbH, CEREC 3D, Manuel utiiisateur, Version 2.0X (in French), 2003,114 pages total.
Stoll et al., "Computer-aided Technologies in Dentistry," (article summary in English, article in German), Dtsch Zahna'rztl Z 45, pp. 314-322 (1990).
Sturman, "Interactive Keyframe Animation of 3-D Articulated Models," Proceedings Graphics Interface '84, May-Jun. 1984, pp. 35-40.
The Choice Is Clear: Red, White & Blue . . . The Simple, Affordable, No-Braces Treatment, Allesee Orthodontic Appliances—Pro Lab product information for doctors. http://ormco.com/aoa/appliancesservices/RWB/doctorhtml>, 5 pages (May 19, 2003).
The Choice is Clear: Red, White & Blue . . . The Simple, Affordable, No-Braces Treatment, Allesee Orthodontic Appliances—Pro Lab product information for patients, <http://ormco.com/aoa/appliancesservices/RWB/patients.html>, 2 pages (May 19, 2003).
The Choice Is Clear: Red, White & Blue . . . The Simple, Affordable, No-Braces Treatment, Allesee Orthodontic Appliances—Pro Lab product information, 6 pages (2003).
The Red, White & Blue Way to Improve Your Smile! Allesee Orthodontic Appliances—Pro Lab product information for patients, 2 pages 1992.
Truax L., "Truax Clasp-Less(TM) Appliance System," Funct. Orthod., 9(5):22-4, 26-8 (Sep.-Oct. 1992).
TRU-TAIN Orthodontic & Dental Supplies, Product Brochure, Rochester, Minnesota 55902, 16 pages total (1996).
U.S. Department of Commerce, National Technical Information Service, "Automated Crown Replication Using Solid Photography SM," Solid Photography Inc., Melville NY, Oct. 1977, 20 pages total.

(56) References Cited

OTHER PUBLICATIONS

U.S. Department of Commerce, National Technical Information Service, "Holodontography: An Introduction to Dental Laser Holography," School of Aerospace Medicine Brooks AfB Tex, Mar. 1973, 37 pages total.
U.S. Appl. No. 60/050,342, filed Jun. 20, 1997, 41 pages total.
Van Der Linden et al., "Three-Dimensional Analysis of Dental Casts by Means of the Optocom," J. Dent. Res., p. 1100 (Jul.-Aug. 1972).
Van Der Linden, "A New Method to Determine Tooth Positions and Dental Arch Dimensions," J. Dent. Res., 51(4):1104 (Jul.-Aug. 1972).
Van Der Zel, "Ceramic-Fused-to-Metal Restorations with a New CAD/CAM System," Quintessence Int., 24(11):769-778 (1993).
Varady et al., "Reverse Engineering of Geometric Models—An Introduction," Computer-Aided Design, 29(4):255-268,1997.
Verstreken et al., "An Image-Guided Planning System for Endosseous Oral Implants," IEEE Trans. Med. Imaging, 17(5):842-852 (Oct. 1998).
Warunek et al., Physical and Mechanical Properties of Elastomers in Orthodonic Positioners, Am J. Orthod. Dentofac. Orthop. vol. 95, No. 5, (May 1989) pp. 399-400.
Warunek et.al., Clinical Use of Silicone Elastomer Applicances, JCO (1989) XXIII(10):694-700.
Wells, Application of the Positioner Appliance in Orthodontic Treatment, Am. J. Orthodont. (1970) 58:351-366.
Williams, "Dentistry and CAD/CAM: Another French Revolution," J. Dent. Practice Admin., pp. 2-5 (Jan./Mar. 1987).
Williams, "The Switzerland and Minnesota Developments in CAD/CAM," J. Dent. Practice Admin., pp. 50-55 (Apr./Jun. 1987).
Wishan, "New Advances in Personal Computer Applications for Cephalometric Analysis, Growth Prediction, Surgical Treatment Planning and Imaging Processing," Symposium: Computerized Facial Imaging in Oral and Maxilofacial Surgery Presented on Sep. 13, 1990.
WSCG'98—Conference Program, "The Sixth International Conference in Central Europe on Computer Graphics and Visualization '98," Feb. 9-13, 1998, pp. 1-7, retrieved from the Internet on Nov. 5, 2004, URL<http://wscg.zcu.cz/wscg98/wscg98.h>.
Xia et al., "Three-Dimensional Virtual-Reality Surgical Planning and Soft-Tissue Prediction for Orthognathic Surgery," IEEE Trans. Inf. Technol. Biomed., 5(2):97-107 (Jun. 2001).
Yamamoto et al., "Optical Measurement of Dental Cast Profile and Application to Analysis of Three-Dimensional Tooth Movement in Orthodontics," Front. Med. Biol. Eng., 1(2):119-130 (1988).
Yamamoto et al., "Three-Dimensional Measurement of Dental Cast Profiles and Its Applications to Orthodontics," Conf. Proc. IEEE Eng. Med. Biol. Soc., 12(5):2051-2053 (1990).
Yamany et al., "A System for Human Jaw Modeling Using Intra-Oral Images," Proc. of the 20th Annual Conf. of the IEEE Engineering in Medicine and Biology Society, Nov. 1, 1998, vol. 2, pp. 563-566.
Yoshii, "Research on a New Orthodontic Appliance: The Dynamic Positioner (D.P.); I. The D.P. Concept and Implementation of Transparent Silicone Resin (Orthocon)," Nippon Dental Review, 452:61-74 (Jun. 1980).
Yoshii, "Research on a New Orthodontic Appliance: The Dynamic Positioner (D.P.); II. The D.P. Manufacturing Procedure and Clinical Applications," Nippon Dental Review, 454:107-130 (Aug. 1980).
Yoshii, "Research on a New Orthodontic Appliance: The Dynamic Positioner (D.P.); III.—The General Concept of the D.P. Method and Its Therapeutic Effect, Part 2. Skeletal Reversed Occlusion Case Reports," Nippon Dental Review, 458:112-129 (Dec. 1980).
Yoshii, "Research on a New Orthodontic Appliance: The Dynamic Positioner (D.P.); III. The General Concept of the D.P. Method and Its Therapeutic Effect, Part 1, Dental and Functional Reversed Occlusion Case Reports," Nippon Dental Review, 457:146-164 (Nov. 1980).
You May Be a Candidate for This Invisible No-Braces Treatment, Allesee Orthodontic Appliances—Pro Lab product information for patients, 2 pages (2002).

\* cited by examiner

REINFORCED ALIGNER HOOKS

CROSS-REFERENCE

This application is a divisional application of Ser. No. 12/772,130, filed Apr. 30, 2010, now abandoned, which is incorporated herein by reference in its entirety and to which application we claim priority under 35 U.S.C. § 120.

BACKGROUND

The present invention relates generally to the field of orthodontics, and more particularly to dental positioning appliances configured to interface with an orthodontic elastic member and react a force from the elastic member into the appliance.

An objective of orthodontics is to move a patient's teeth to positions where function and/or aesthetics are optimized. Traditionally, appliances such as braces are applied to a patient's teeth by a treating practitioner and the set of braces exerts continual force on the teeth and gradually urges them toward their intended positions. Over time and with a series of clinical visits and adjustments to the braces, the practitioner adjusts the appliances to move the teeth toward their final destination.

More recently, alternatives to conventional orthodontic treatment with traditional affixed appliances (e.g., braces) have become available. For example, systems including a series of preformed appliances/aligners have become commercially available from Align Technology, Inc., Santa Clara, Calif., under the tradename Invisalign® System. The Invisalign® System is described in numerous patents and patent applications assigned to Align Technology, Inc. including, for example in U.S. Pat. Nos. 6,450,807, and 5,975,893, as well as on the company's website, which is accessible on the World Wide Web (see, e.g., the url "www.invisalign.com"). The Invisalign® System includes designing and/or fabricating multiple, and sometimes all, of the aligners to be worn by the patient before the aligners are administered to the patient and used to reposition the teeth (e.g., at the outset of treatment). Often, designing and planning a customized treatment for a patient makes use of computer-based 3-dimensional planning/design tools, such as Treat™ software from Align Technology, Inc. The design of the aligners can rely on computer modeling of a series of planned successive tooth arrangements, and the individual aligners are designed to be worn over the teeth and elastically reposition the teeth to each of the planned tooth arrangements.

While recently developed orthodontic treatment technologies, such as those described above, represent a considerable advancement in the field of orthodontics, additional advancements remain of interest. For example, in some instances it may be advantageous to use an orthodontic elastic member to generate a tension force between a patient's upper and lower teeth to bring the teeth into a desired occlusion. In some traditional approaches, brackets are bonded to the teeth and an orthodontic elastic member is used to couple the brackets to generate the tension force. Generating such a tension force in conjunction with recently developed orthodontic approaches can be challenging. For example, shell aligners are generally designed to match the geometry of a patient's teeth, thereby leaving little room for bonding such brackets to a patient's teeth. As such, there is a need for shell aligners that can be used in conjunction with an orthodontic elastic member to, for example, bring a patient's teeth into a desired occlusion.

BRIEF SUMMARY

The present disclosure provides orthodontic positioning appliances for use with an orthodontic elastic member, and related systems and methods. The disclosed positioning appliances are configured to couple with an orthodontic elastic member so as to react a force from the elastic member into the appliance. Such appliances can advantageously employ the force imparted by the elastic member to apply desired repositioning forces to a patient's teeth to, for example, generate a desired occlusion and/or supplement repositioning forces generated by the appliance.

For a fuller understanding of the nature and advantages of the present invention, reference should be made to the ensuing detailed description and accompanying drawings. Other aspects, objects and advantages of the invention will be apparent from the drawings and detailed description that follows.

DETAILED DESCRIPTION

Figure 1:
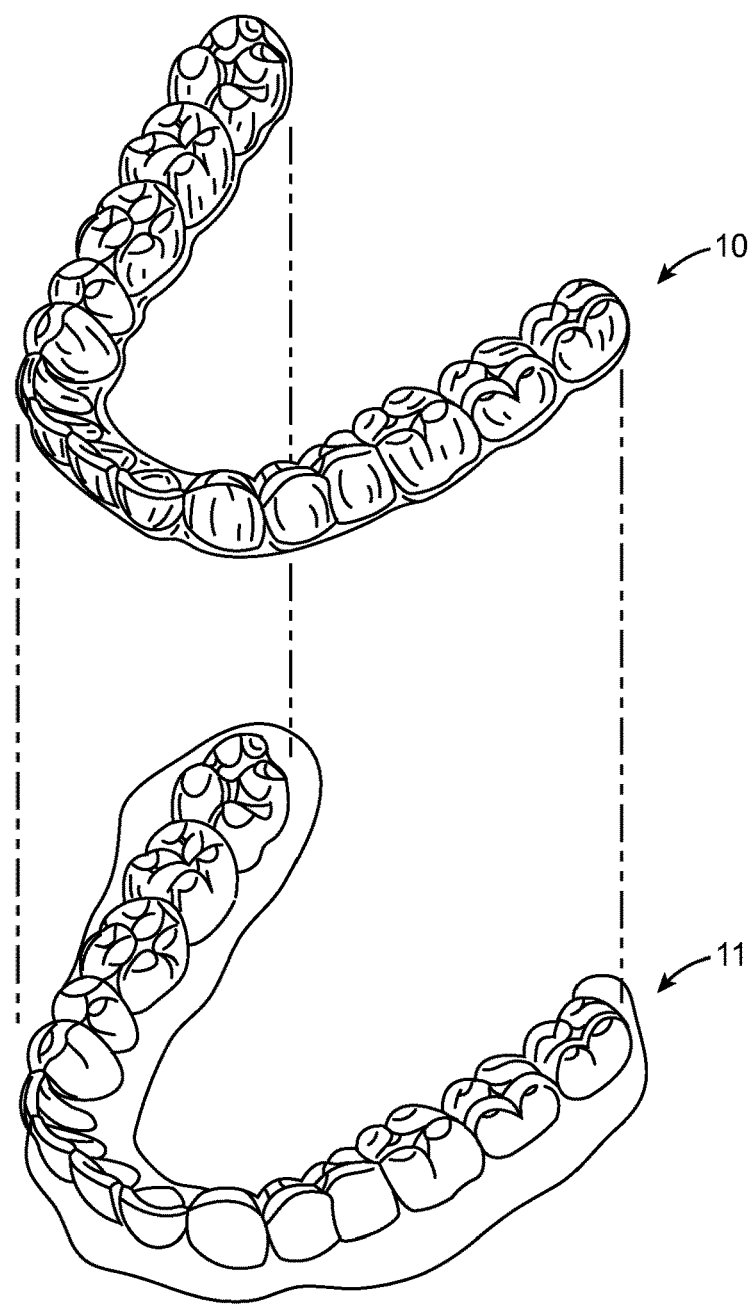
FIG. 1 illustrates a jaw and an incremental positioning appliance for the jaw, in accordance to an embodiment.

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Orthodontic positioning appliances are provided that can be used in conjunction with one or more orthodontic elastic members, as well as related methods and systems. During orthodontic treatment, it may be necessary to apply forces to a tooth to generate movement of the tooth to, for example, bring the patient's teeth into a better occlusion. The presently disclosed appliances, methods, and systems provide means by which such forces can be applied during orthodontic treatment where appliances having teeth receiving cavities are used, such as preformed appliances/aligners available from Align Technology, Inc., Santa Clara, Calif., under the tradename Invisalign® System.

The disclosed orthodontic positioning appliances for use with an orthodontic elastic member include, for example, a patient removable tooth positioning appliance having teeth receiving cavities shaped to receive and apply a resilient positioning force to a patient's teeth. The positioning appliance can include a hook configured to interface with an orthodontic elastic member so as to react a force from the elastic member into the patient-worn appliance, thereby applying (e.g., supplementing) forces other than or in addition to the forces applied to the patient's teeth and generated solely by the positioning appliance(s) in the absence of the coupled elastic member. The appliance and/or hook thereof can be configured to more optimally engage an elastic member when the appliance is worn by the patient. In one embodiment, for example, the hook can be configured to be laterally offset from another portion of the appliance, such as a portion of the appliance that engages the patients teeth when worn. For example, a hook can be offset (e.g., laterally offset) from a portion of the appliance that engages a buccal surface of a tooth when the appliance is coupled with the patient's teeth. In such an embodiment, the hook will be offset even when no orthodontic elastic member is coupled with the tooth.

In another embodiment, an appliance can be configured such that the hook is gingivally offset from a portion of the appliance. For example, certain shell-type appliances will include a gingival edge or edge of the appliance that, when worn by a patient, is disposed substantially along the gingival line or margin where gingival tissue meets the tooth crown at the base of the tooth. In certain embodiments, a hook of an appliance will be gingivally offset or offset in a gingival direction relative to the gingival edge of the appliance. Such a configuration advantageously allows incorporation of the hook into the appliance structure, but without necessarily reducing tooth receiving/engaging surfaces of an appliance cavity.

An appliance can include a reinforcement structure selected and/or disposed on the appliance so as to stiffen the appliance against lateral deflection induced by the force from the elastic member. For example, a portion of the appliance can include a corrugation to stiffen the appliance. In another embodiment, the appliance can include a locally stiffened area (e.g., via an added shape or contour) connected with the hook to stiffen the hook against deflection (e.g., lateral deflection) induced by the force from the elastic member.

Referring now to the drawings, in which like reference numerals represent like parts throughout the several views, FIG. 1 provides an appropriate starting point in a discussion of the present invention with respect to tooth repositioning appliances designed to apply repositioning forces to teeth. A tooth repositioning appliance 10 can be worn by a patient in order to achieve an incremental repositioning of individual teeth in the jaw 11. The appliance can include a shell (e.g., polymeric shell) having teeth-receiving cavities that receive and resiliently reposition the teeth. In many embodiments, a polymeric appliance can be formed from a thin sheet of suitable elastomeric polymeric material, such a 0.03 inch thermal forming dental material by Tru-Tain Plastics, Rochester, Minn. An appliance can fit over all teeth present in an upper or lower jaw, or less than all of the teeth. In some cases, only certain teeth received by an appliance will be repositioned by the appliance while other teeth can provide a base or anchor region for holding the appliance in place as it applies force against the tooth or teeth targeted for repositioning. In some cases, many or most, and even all, of the teeth will be repositioned at some point during treatment. Teeth that are moved can also serve as a base or anchor for holding the appliance as it is worn by the patient. Typically, no wires or other means will be provided for holding an appliance in place over the teeth. In some cases, however, it may be desirable or necessary to provide individual anchors on teeth with corresponding receptacles or apertures in the appliance so that the appliance can apply a selected force on the tooth. Exemplary appliances, including those utilized in the Invisalign® System, are described in numerous patents and patent applications assigned to Align Technology, Inc. including, for example in U.S. Pat. Nos. 6,450,807, and 5,975,893, as well as on the company's website, which is accessible on the World Wide Web (see, e.g., the url "www.invisalign.com").

An appliance can be designed and/or provided as part of a set or plurality of appliances. In such an embodiment, each appliance may be configured so a tooth-receiving cavity has a geometry corresponding to an intermediate or final tooth arrangement intended for the appliance. The patient's teeth can be progressively repositioned from an initial tooth arrangement to a target tooth arrangement by placing a series of incremental position adjustment appliances over the patient's teeth. A target tooth arrangement can be a planned final tooth arrangement selected for the patient's teeth at the end of all planned orthodontic treatment. Alternatively, a target arrangement can be one of many intermediate arrangements for the patient's teeth during the course of orthodontic treatment, which may include where surgery is recommended, where inter-proximal reduction (IPR) is appropriate, where a progress check is scheduled, where anchor placement is best, where palatal expansion is desirable, etc. As such, it is understood that a target tooth arrangement can be any planned resulting arrangement for the patient's teeth that follows one or more incremental repositioning stages. Likewise, an initial tooth arrangement can be any initial arrangement for the patient's teeth that is followed by one or more incremental repositioning stages. The adjustment appliances can be generated all at the same stage or in sets or batches, e.g., at the beginning of a stage of the treatment, and the patient wears each appliance until the pressure of each appliance on the teeth can no longer be felt or has resulted in the maximum amount of expressed tooth movement for that given stage. A plurality of different appliances (e.g., set) can be designed and even fabricated prior to the patient wearing any appliance of the plurality. After wearing an appliance for an appropriate period of time, the patient replaces the current appliance with the next appliance in the series until no more appliances remain. The appliances are generally not affixed to the teeth and the patient may place and replace the appliances at any time during the procedure (e.g., patient-removable appliances). The final appliance or several appliances in the series may have a geometry or geometries selected to overcorrect the tooth arrangement, i.e., have a geometry which would (if fully achieved) move individual teeth beyond the tooth arrangement which has been selected as the "final." Such over-correction may be desirable in order to offset potential relapse after the repositioning method has been terminated, i.e., to permit movement of individual teeth back toward their pre-corrected positions. Over-correction may also be beneficial to speed the rate of correction, i.e., by having an appliance with a geometry that is positioned beyond a desired intermediate or final position, the individual teeth will be shifted toward the position at a greater rate. In such cases, the use of an appliance can be terminated before the teeth reach the positions defined by the appliance.

During a course of orthodontic treatment, it may be necessary to apply a force to a patient's teeth to generate movement of the tooth to bring the patient's teeth into a better occlusion. In many instances, it may not be possible to generate desired levels of such a force solely through the use of a tooth positioning appliance such as the tooth positioning appliance 10 described above. The forces generated by such a tooth positioning appliance can, however, be supplemented by the use of an orthodontic elastic member.

In accordance with an embodiment of the present invention, an orthodontic appliance, such as those described above, can be designed/configured for use in engagement with one or more elastic members. Such an appliance, can be configured to include one or more hooks for engagement with one or more elastic members. And a set of appliances can include one or more appliances with hooks.

Figure 2A:
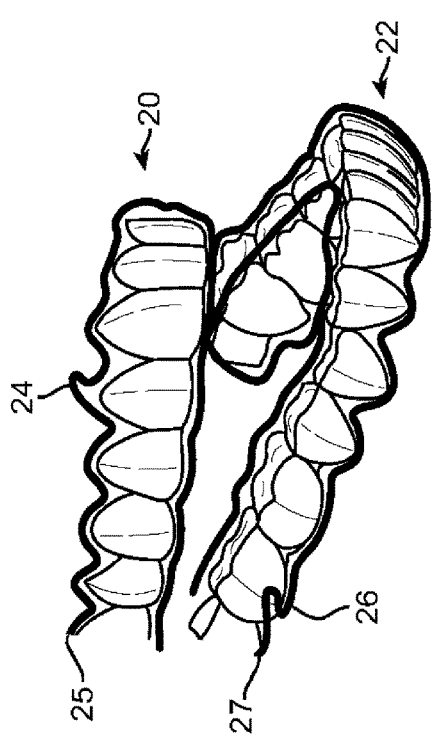
FIG. 2A illustrates upper and lower teeth received within incremental tooth positioning appliances having gingivally disposed hooks, in accordance to an embodiment.

FIG. 2A illustrates tooth positioning appliances 20, 22 for receiving, respectively, upper and lower teeth of a patient. Appliances 20, 22 include hooks 24, 26, respectively. Appliance 20 includes a gingival edge 25 of the appliance that substantially follows along a gingival margin of the patient's dentition as the appliance 20 is worn. Similarly, appliance 22 includes a gingival edge 27. The hooks 24, 26 extend gingivally or in a gingival direction relative to gingival edge 25, 27, respectively, and may be pointed in a mesial, distal, or vertical direction In the illustrated embodiment, hook 24 is pointed mesially and hook 26 is pointed distally. As noted above, such a gingivally offset configuration can maximize the surface area of the aligner material engaging the tooth received in an adjacent tooth receiving cavity. Hooks 24, 26 may further be offset laterally, e.g., to better accommodate an elastic member engaging the hook, as described further herein. In use, an orthodontic elastic member can be coupled between the hooks 24, 26, thereby applying a reciprocal force to each of the appliances 20, 22. One or more hooks can be incorporated into each of the appliances 20, 22 to apply one or more forces into the appliances. Such forces can be used to supplement the teeth repositioning forces generated, e.g., by engagement between the patient's teeth/tooth surfaces and surfaces of corresponding receiving cavities of the appliances 20, 22.

Figure 2B:
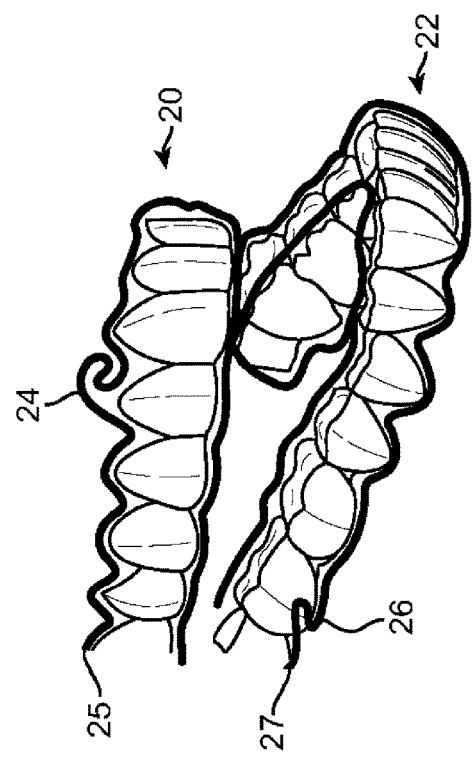
FIG. 2B illustrates upper and lower teeth received within incremental tooth positioning appliances having gingivally disposed hooks, wherein the hooks are configured to angle or curve more toward a tooth's surface, in accordance with an embodiment.

FIG. 2B illustrates positioning appliances 20, 22. The appliances 20, 22 include hooks 24, 26, respectively, wherein the hooks 24, 26 angle or curve back more toward tooth's surfaces compared to the embodiment illustrated in FIG. 2A. Hooks as in FIG. 2B may be selected, for example, to better avoid unwanted contact or poking of the patient's soft tissue.

Figure 3A:
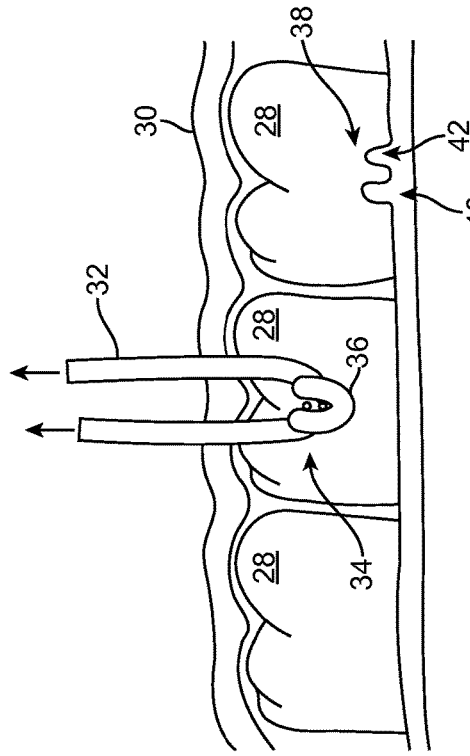
FIG. 3A illustrates teeth received within teeth receiving cavities of an incremental tooth positioning appliance and an orthodontic elastic member coupled with the positioning appliance. The appliance includes notches or hooks cut or formed into a tooth receiving cavity of the appliance.

FIG. 3A illustrates teeth 28 received within teeth receiving cavities of an incremental tooth positioning appliance 30. An orthodontic elastic member 32 is coupled with the tooth positioning appliance 30 via a hook 34 formed by creating a u-shaped aperture 36 located in the side of the appliance. The aperture 36 can be formed into an existing appliance at a location selected for the transfer of the force from the elastic member into the appliance. The aperture 36 can have a slot width and a shape selected to accommodate the elastic member. A hook 38 can also be positioned along a gingival margin of the appliance 30. The hook 38 can be formed, for example, via adjacent slots 40, 42 formed in the gingival margin of the appliance 30. Hooks 34 and 38 may be formed by simply cutting or trimming out material from a shell appliance. However, hooks formed by such an approach reduce appliance material or surfaces engaging a tooth received within an adjacent cavity and require deflection of appliance material forming the hook in order to accommodate a positioned elastic member (see, e.g., FIG. 3B).

Figure 3B:
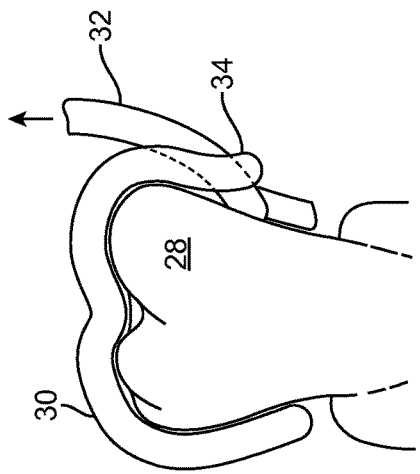
FIG. 3B is a cross-sectional view of a tooth and the positioning appliance of FIG. 3A illustrating hook displacement induced by the orthodontic elastic member.

FIG. 3B is a cross-sectional view of a tooth 28 and the positioning appliance 30 of FIG. 2A. Because the hook 34 is formed via the u-shaped aperture, when the elastic member 32 is coupled with the hook 34, the hook is forced to deflect away from the adjacent surface of the tooth 28 to accommodate the presence of the elastic member 32 between the hook 34 and the tooth 28. Additional deflection of the hook 34 may be induced by the force imparted into the hook by the elastic member 32. Such additional deflections can be controlled to some extent by shaping the overall width of the u-shaped aperture to produce a wider hook.

Figure 4A:
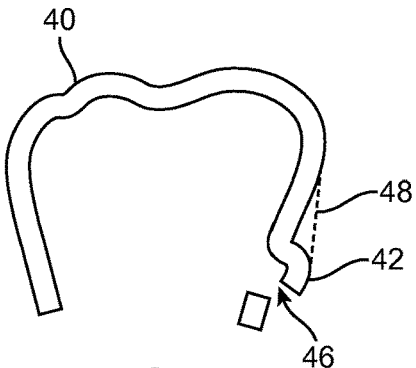
FIG. 4A is a cross-sectional view of an incremental tooth positioning appliance having an offset hook, in accordance with an embodiment of the present invention.
Figure 4B:
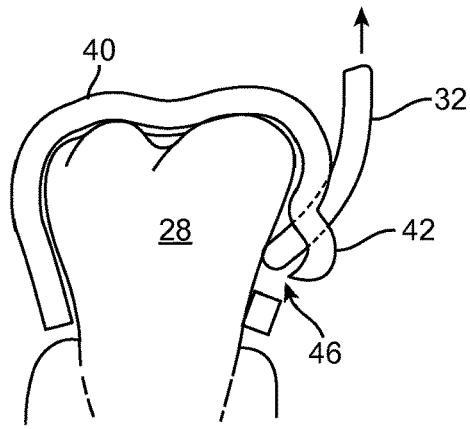
FIG. 4B illustrates a tooth received within a tooth receiving cavity of the incremental tooth positioning appliance of FIG. 4A and an orthodontic elastic member coupled with the offset hook, in accordance with an embodiment of the present invention.

FIG. 4A illustrates an incremental tooth positioning appliance 40 having an offset hook 42. FIG. 4B illustrates a tooth 28 received within a tooth receiving cavity of the incremental tooth positioning appliance 40 and an orthodontic elastic member 32 coupled with the offset hook 42. The offset hook 42 is offset from an adjacent surface of the tooth 28 (e.g., buccal surface, lingual surface) when the appliance 40 is coupled with the patient's teeth and no orthodontic elastic member is coupled with the hook. The offset can be configured to accommodate an elastic member with reduced deflection, in contrast to the hook 34 or 38 of FIGS. 3A and 3B. The hook 42 can be shaped to retain the elastic member in the absence of the elastic member being coupled with an opposing arch of the patient teeth. For example, the hook 42 can be shaped to trap the elastic member in contact with the surface of the tooth 28 (e.g., via a hook shaped to engage a sufficient portion of the perimeter of the elastic member), while still allowing installation of the elastic member into the trapping engagement of the hook 42 via an opening 46. The lateral offset may be configured such that the opening 46 is closer to the tooth than the maximum offset distance, in order that the offset allows the elastic to be engaged against the aligner without touching the tooth, but the hook does not protrude towards the soft tissue, thereby making the hook comfortable for the patient.

In one example, the tip of the hook may curve or angle away from soft tissue or back toward the tooth surface. The tip of the hook may also be curved, angled, or bent towards the gingival line such that the elastic may be placed into the aligner first before the aligner is worn, and the hook angle/curvature keeps the elastic from falling off of the aligner.

Figure 4C:
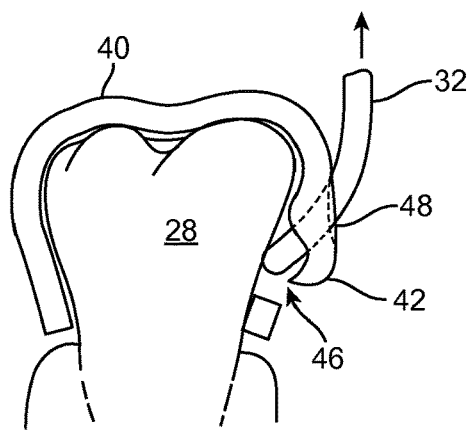
FIG. 4C illustrates a reinforced version of the offset hook of FIG. 4A, in accordance with an embodiment of the present invention.

The appliance 40 can optionally include a reinforcement structure in the vicinity of the hook 42 to reduce deflection induced by the force from the elastic member 32. For example, as illustrated in FIG. 4C, the appliance 40 can include a locally strengthened region 48 (e.g., via increased thickness in the area of the hook). The appliance 40 can also be locally stiffened by embedding a reinforcing structure (e.g., a stronger and stiffer material such as stainless steel or plastic resin filler) into the appliance to reinforce the appliance/hook against deflection induced by the force from the elastic member.

Figure 5:
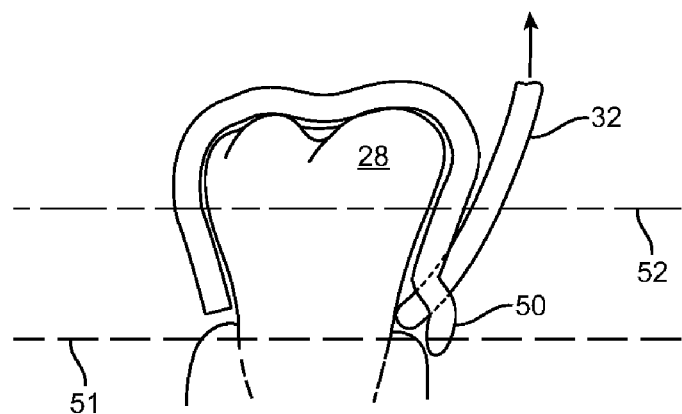
FIG. 5 illustrates a tooth received within a tooth receiving cavity of an incremental tooth positioning appliance having a gingivally disposed offset hook and an orthodontic elastic member coupled with the gingivally disposed hook, in accordance with an embodiment of the present invention.
Figure 6:
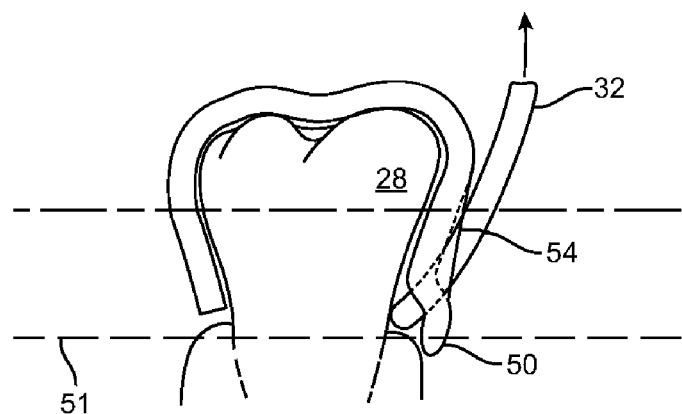
FIG. 6 illustrates a reinforced version of the gingivally disposed hook of FIG. 5, in accordance with an embodiment of the present invention.

As illustrated in FIG. 5, an offset hook 50 can also be disposed gingivally offset relative to a center of a clinical crown 52 of a tooth 28 as received in a cavity proximate to the hook 50, and may be gingivally offset relative to a gingival edge of the appliance or a gingival margin or line 51 identifying or approximating where gingival tissue meets the base of the tooth 28 crown. Such a gingival offset can be used to increase the surface area of the positioning appliance that engages the tooth 28, as well as to provide space for accommodating an elastic member 32 without necessarily requiring lateral deflection for elastic member engagement. As illustrated in FIG. 6, an appliance having such a gingivally offset hook 50 can include a locally reinforced area 54 (e.g., the appliance can be locally thickened in the vicinity of the offset hook) to reduce deflection of the hook 50 induced by the force from the elastic member. The appliance can also be locally stiffened by embedding a reinforcing structure (e.g., a stronger and stiffer material such as stainless steel or plastic resin) into the appliance to reinforce the appliance/hook against deflection induced by the force from the elastic member.

Figure 7:
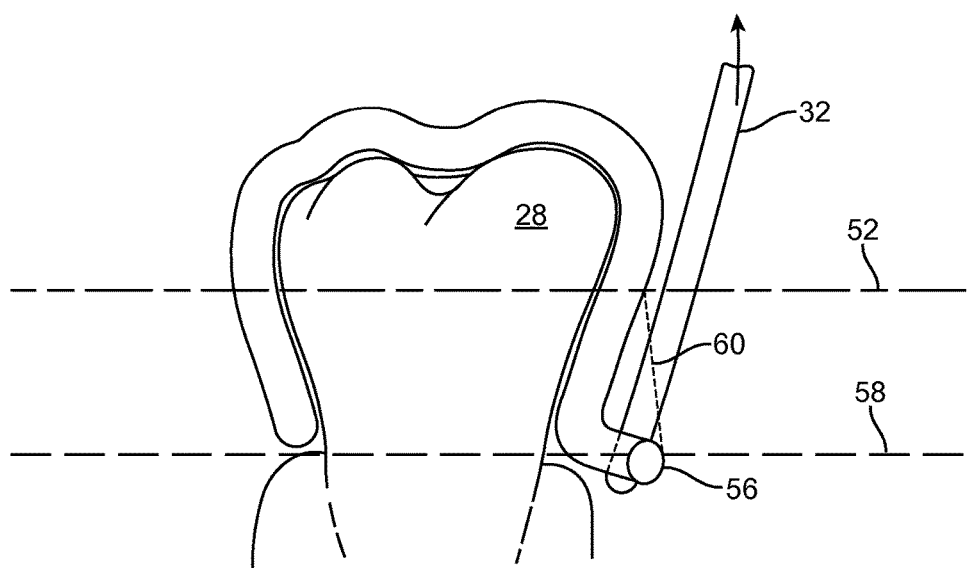
FIG. 7 illustrates a tooth received within a tooth receiving cavity of an incremental tooth positioning appliance having a gingivally disposed offset hook and an orthodontic elastic member coupled with the gingivally disposed hook, in accordance with an embodiment of the present invention.

FIG. 7 illustrates an offset hook 56 that is disposed even more gingivally offset relative to the center of a clinical crown 52 of a tooth 28 received in a cavity proximate to the hook 56 than the hook 50 shown in FIGS. 5 and 6. In addition to being more gingivally offset, the hook 56 is also offset further from the adjacent surface of the tooth 28 in order to be disposed at or below a gingival line 58 for the tooth 28. The appliance having such a gingivally offset hook 56 can include a locally reinforced area 60 (e.g., the appliance can be locally thickened in the vicinity of the offset hook) to reduce deflection of the hook 56 induced by the force from the elastic member 32.

Figure 8A:
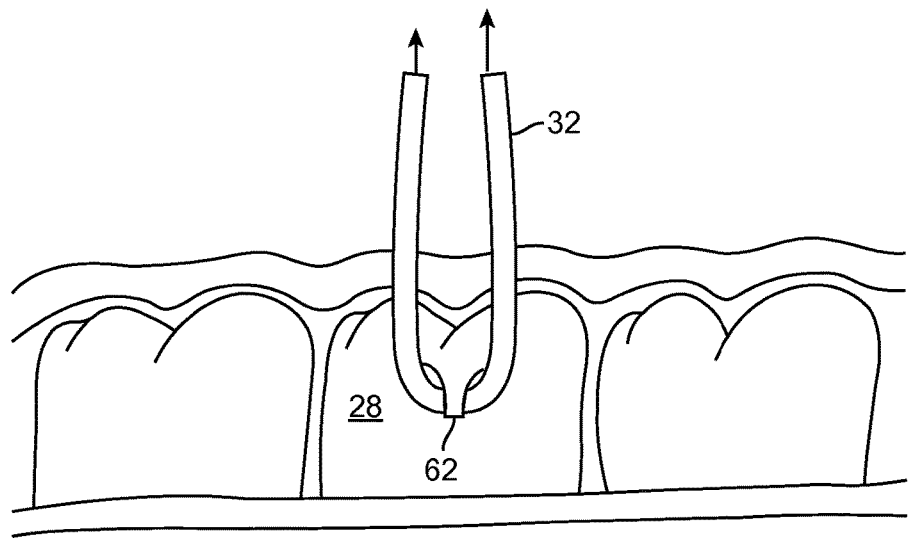
FIG. 8A illustrates teeth received within teeth receiving cavity of an incremental tooth positioning appliance having an exterior hook and an orthodontic elastic member coupled with the exterior hook, in accordance with an embodiment of the present invention.
Figure 8B:
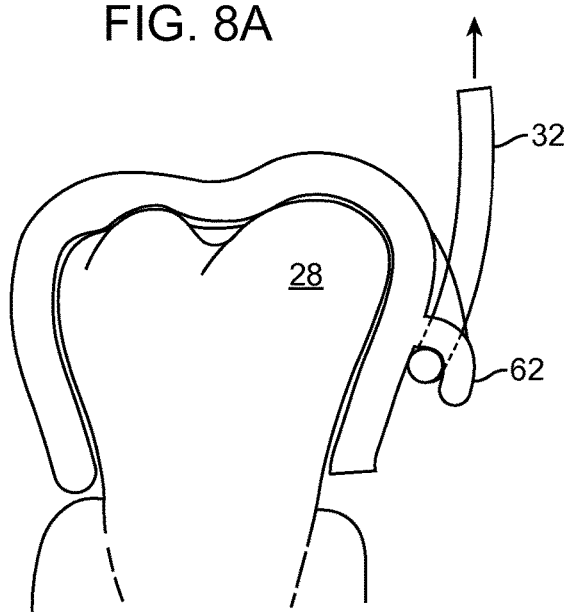
FIG. 8B is a cross-sectional view of a tooth and the positioning appliance of FIG. 8A illustrating the orthodontic elastic member coupled with the exterior hook, in accordance with an embodiment of the present invention.
Figure 9A:
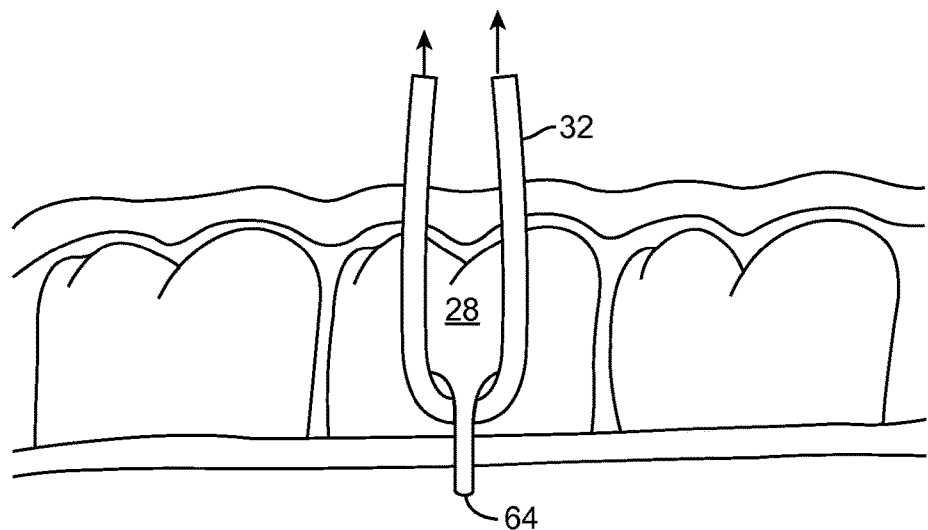
FIG. 9A illustrates teeth received within teeth receiving cavities of an incremental tooth positioning appliance having a gingivally disposed exterior hook and an orthodontic elastic member coupled with the gingivally disposed exterior hook, in accordance with an embodiment of the present invention.
Figure 9B:
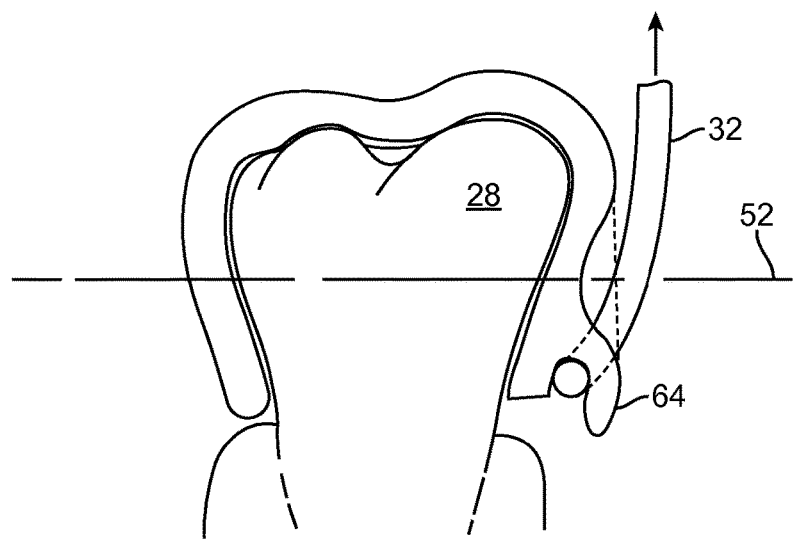
FIG. 9B is a cross-sectional view of a tooth and the positioning appliance of FIG. 9A illustrating the orthodontic elastic member coupled with the gingivally disposed exterior hook, in accordance with an embodiment of the present invention.

An appliance can be configured with an exterior offset hook that couples with an elastic member such that the elastic member does not contact a surface of the tooth. FIGS. 8A and 8B illustrate an exterior offset hook 62 positioned similar to the offset hook 42 illustrated in FIGS. 4A through 4C. FIGS. 9A and 9B illustrate an exterior offset hook 64 offset gingivally similar to the offset hook illustrated in FIGS. 5 and 6. A positioning appliance can be configured with such an exterior offset hook by incorporating additional material on the exterior of a basic positioning appliance such as the appliance 10 illustrated in FIG. 1. Exterior hooks can also be locally reinforced, for example, via locally thickened areas as illustrated in FIGS. 8B and 9B.

Figure 10:
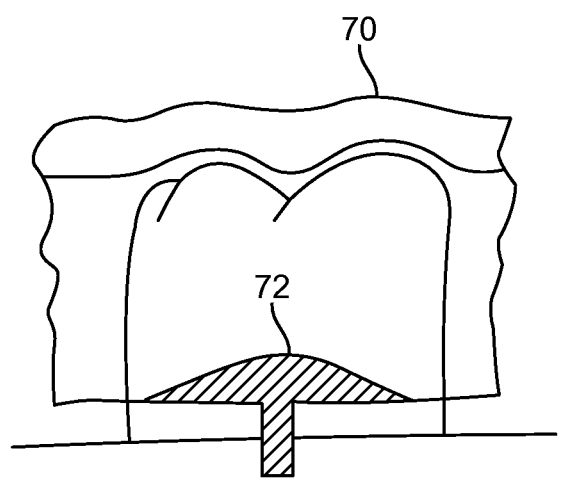
FIG. 10 illustrates an incremental tooth positioning appliance having a reinforcing corrugation and an exterior hook coupled with an orthodontic elastic member, in accordance with an embodiment of the present invention.

A tooth repositioning appliance can also include a reinforcement structure to stiffen the appliance against deflection induced by the force from an elastic member. For example, FIG. 10 illustrates a repositioning appliance 70 having a reinforcing corrugation 72 formed along a gingival edge of the repositioning appliance. The corrugation 72 can be formed by adding an elongated protrusion to a male mold prior to forming the appliance over the male mold. A corrugation can be used to stiffen the gingival edge of the repositioning appliance against lateral deflection induced by the force from the elastic member 32.

The present invention further provides methods for using one or more orthodontic positioning devices having one or more hooks configured to interface with an orthodontic elastic member so as to react a force from the elastic member into the patient-worn device. The above-described orthodontic positioning devices can be configured for use in practicing orthodontic treatment or tooth repositioning methods. For example, a first orthodontic positioning device can be provided, the device having a hook configured to interface with an orthodontic elastic member is received (e.g., by a patient, by a dental professional, etc.), e.g., as described above. The first positioning device is coupled with a first arch of the patient's teeth. An orthodontic elastic member is coupled with the hook of the first positioning device to transfer a force from the elastic member into the first positioning device. A second orthodontic positioning device having a hook configured to interface with an orthodontic elastic member is received. The second orthodontic positioning device is coupled with a second arch of the patient's teeth, and the orthodontic elastic member that is coupled with the hook of the first positioning device is coupled with the hook of the second positioning device. Methods can include use of a plurality of different (e.g., successive) positioning devices or appliances.

The present invention further provides systems for repositioning a patient's teeth. A system can include a plurality of orthodontic tooth positioning appliances. Consistent with discussion provided further herein, at least two of the appliances can have different teeth receiving cavities shaped to receive and resiliently reposition the patient's teeth in a first arch of the patient's teeth from a first arrangement to a successive arrangement. At least one of the appliances includes a hook configured to interface with an orthodontic elastic member so as to react a force from the elastic member into the patient-worn appliance. The hook can be configured to be offset from a surface of a tooth when the appliance is coupled with the patient's teeth in the first arch and no orthodontic elastic member is coupled with the hook.

A system can include a plurality appliances, or sets of appliances, for repositioning a patient's upper and lower arch teeth. For example, one of a plurality of upper arch appliances and one of a plurality of lower arch appliances can be configured to be worn simultaneously and coupled with each other via an orthodontic elastic member coupling the hook of the upper arch appliance to the hook of the lower arch appliance. The elastic member may also be coupled within the same arch in order to connect the elastic to an elastic hook that may be directly bonded to an exposed tooth elsewhere in the arch, whereby the aligner has been cut around that tooth-affixed elastic hook. The elastic member may also be coupled from the aligner to an anchorage device attached somewhere in the mouth such as a mini-implant or temporary anchorage device (TAD) affixed to the patient's jaw structure.

The present invention further provides methods, such as a computer-implemented methods, for designing an orthodontic positioning device having teeth receiving cavities. Such a method can be used to design the above-described orthodontic positioning devices. A method can include providing and/or receiving a digital representation of the patient's teeth in a selected arrangement. The arrangement can be selected to define the shape of teeth receiving cavities shaped to receive and apply a resilient positioning force to a patient's teeth. An appliance can be modeled based on the received representation. The received representation can be used to define the teeth receiving cavities of the appliance. The appliance is modeled to include a hook configured to interface with an orthodontic elastic member so as to react a force from the elastic member into the appliance, including hook designs or configurations as indicated further herein. For example, the modeled hook can be configured such that it is offset (e.g., laterally) from a surface of a tooth when the appliance is coupled with the patient's teeth and no orthodontic elastic member is coupled with the hook. The hook may alternatively or additionally be gingivally offset, e.g., relative to a gingival edge of the model appliance or a gingival line of the patient. A reinforcement structure may further be designed or modeled so as to stiffen the appliance against lateral deflection induced by the force from the elastic member can optionally be modeled into the appliance. The reinforcement structure can include, for example, a corrugation (e.g., positioned along a gingival edge of the appliance to increase the bending stiffness of the gingival edge). The reinforcement structure can include a locally reinforced area (e.g., locally thickened) connected with the hook to stiffen the hook against deflection induced by the force from the elastic member.

An aligner having an exterior hook can be created using automated steps, manual steps, and/or a combination of automated and manual steps. Such steps can include, for example, the removal of material from an aligner assembly (e.g., using a physical cutter such as an end mill, a drill, and a punch; using non-contact removal techniques such as laser cutting, and electrical discharge machining (EDM); using other media such as water jets, hot water, and hot gases); the addition of material to an aligner assembly (e.g., by bonding or attaching a pre-formed feature such as a hook); and/or direct fabrication techniques (e.g., stereo lithography).

Figure 11:
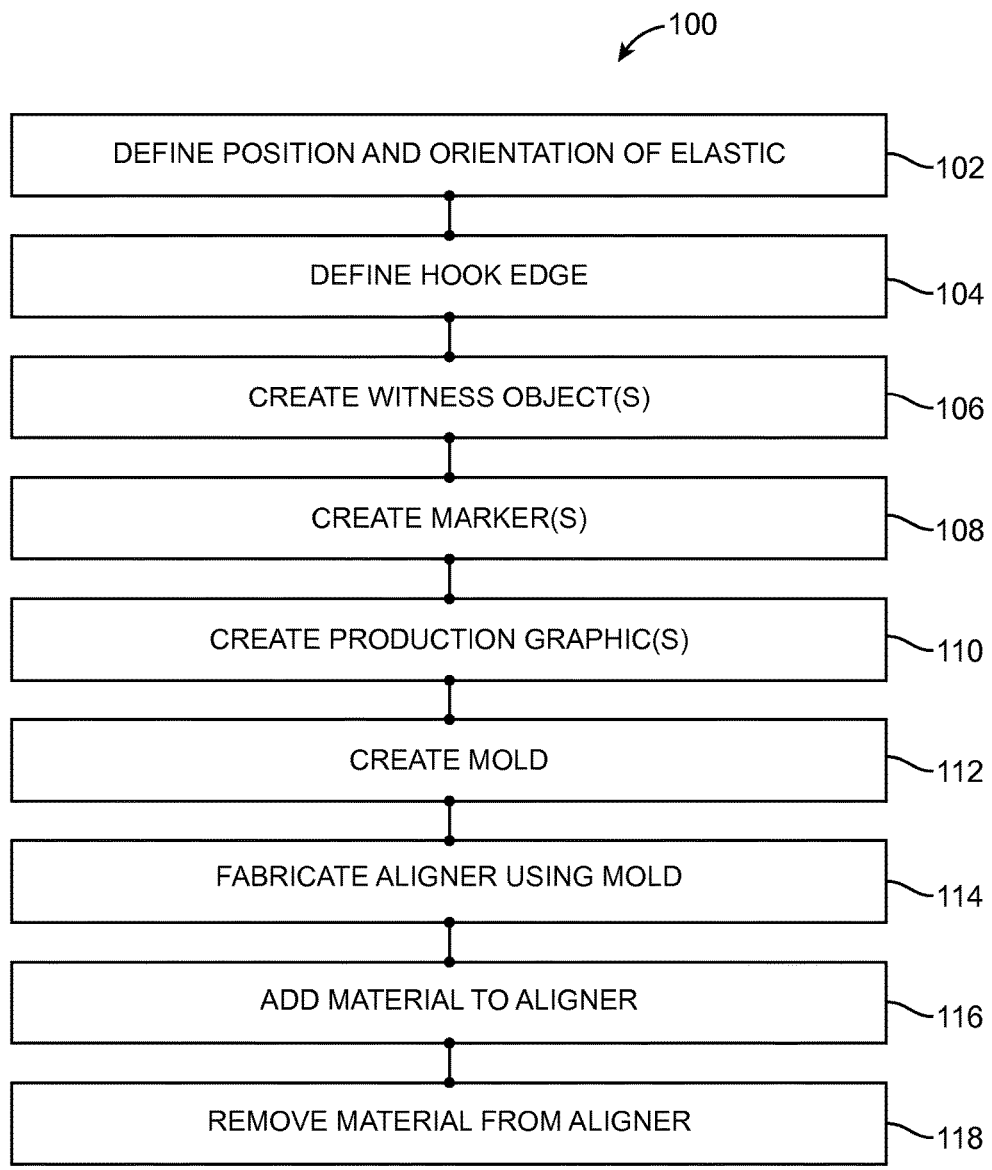
FIG. 11 is a simplified block diagram illustrating a method for fabricating an aligner having an exterior hook using a mold, in accordance with an embodiment of the present invention.

FIG. 11 illustrates a method 100 for indirect fabrication of an aligner having a hook by forming a sheet of material over a mold. The geometry of the mold includes representations of a patient's teeth in an arrangement suitable to generate desired teeth receiving cavities. A witness object is added to the teeth representations to generate an inner surface of an offset hook portion of the aligner. While some of the steps of method 100 are described as being computer-implemented, the alternate use of non-computer implemented approaches may also be apparent to a person of skill in the art. The method 100 can be used to generate the appliances disclosed above.

In step 102, the position and orientation of an elastic member relative to the aligner is defined. The defined position and orientation of the elastic member can be generated, for example, using computer-based 3-dimensional planning/design tools, such as Treat™ from Align Technology, Inc. Computer modeling of one or successive tooth arrangements for a patient's upper and lower teeth can be used to position/orient an elastic member between an upper jaw appliance hook (or a feature attached to an upper jaw tooth) and a lower jaw appliance hook (or a feature attached to a lower jaw tooth). While the elastics shown in the figures are oriented generally vertically, other orientations are possible (e.g., to couple non-occluding pairs of teeth). An elastic member can be positioned so as to generate supplemental forces to treat certain types of malocclusion (e.g., class II and III corrections, canine rotation, extrusion, etc.).

Figure 12A:
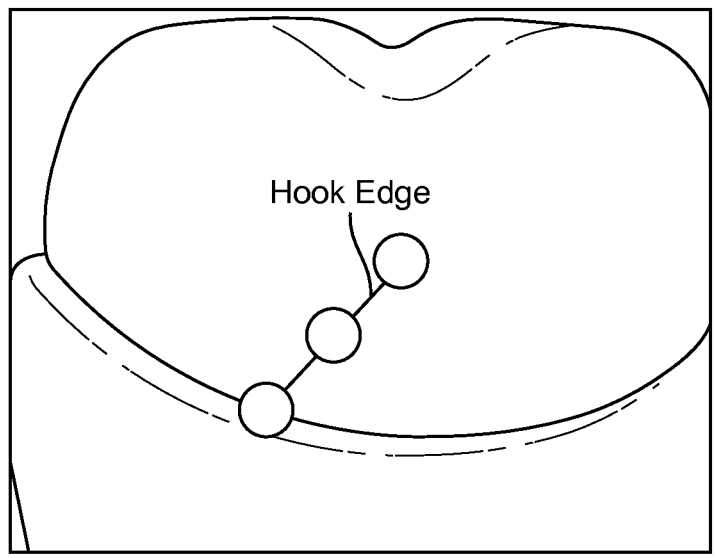
FIGS. 12A and 12B illustrate the addition of a hook edge (12A) and a witness object (12B) to mold geometry used to generate an appliance having an offset hook, in accordance with an embodiment of the present invention.
Figure 12B:
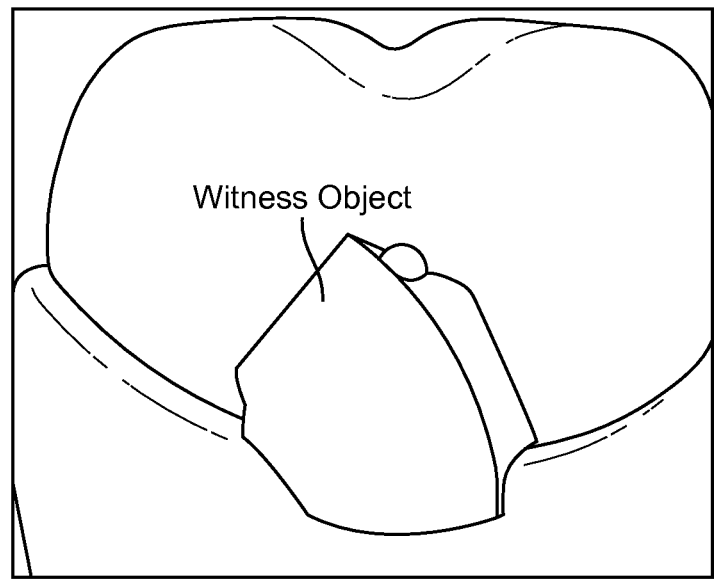

In step 104, a hook edge is defined relative to the mold geometry using the defined position/orientation of the elastic member. The hook edge definition can be a spline on a tooth surface in a 3-dimensional model. The hook edge can be used to position and orient a witness object created in step 106. FIGS. 12A and 12B illustrate a hook edge definition and a witness object positioned and oriented using the hook edge definition and a corresponding tooth surface. The witness object is shaped to generate a suitable offset from the tooth surface to generate a corresponding offset in the inner surface of the aligner. An area of the aligner that will interface with the elastic member to hold the elastic member can be determined. Based on the determined area, the witness object can be created that corresponds to the determined area and merged into the 3-dimensional representation of the patient's teeth. The witness object can be merged into a gingival surface included in the 3-dimensional representation of the patient's teeth, and appropriate smoothing applied. The resulting 3-dimensional representation (mold geometry) can be used to generate a positive mold over which a sheet of material is formed to create an aligner.

In step 108, one or more markers can optionally be created/added to the mold geometry to generate a reference feature(s) in an aligner that can be used to guide subsequent removal of material from the aligner (e.g., see step 118 below) and/or to guide subsequent addition of material to the aligner (e.g., see step 116 below). Further, a production graphic(s) (e.g., a screenshot on a computer monitor or paper) can optionally be generated from the mold geometry in step 110 to, for example, guide subsequent removal of material from the aligner and/or to guide subsequent addition of material to the aligner.

The mold geometry is then used to create a physical mold, which is used to form a sheet of elastomeric material to form the aligner. In step 112, a mold is created from the 3-dimensional mold geometry. The mold can be created, for example, directly using automated fabrication techniques (e.g., stereo lithography). In step 114, the aligner is fabricated by molding a sheet of material over the physical mold.

Once the basic aligner shell is fabricated, material can be optionally added and/or removed from the aligner to finalize the geometry of the hook. In step 116, material can be optionally added to the aligner to, for example, form part or all of the hook structure. For example, a preformed feature can be bonded or otherwise attached to the aligner to serve as the hook. In step 118, material can be optionally removed from the aligner to complete the formation of the offset hook. For example, localized portions of the aligner can be removed to accommodate the elastic member when installed on the hook.

Figure 13:
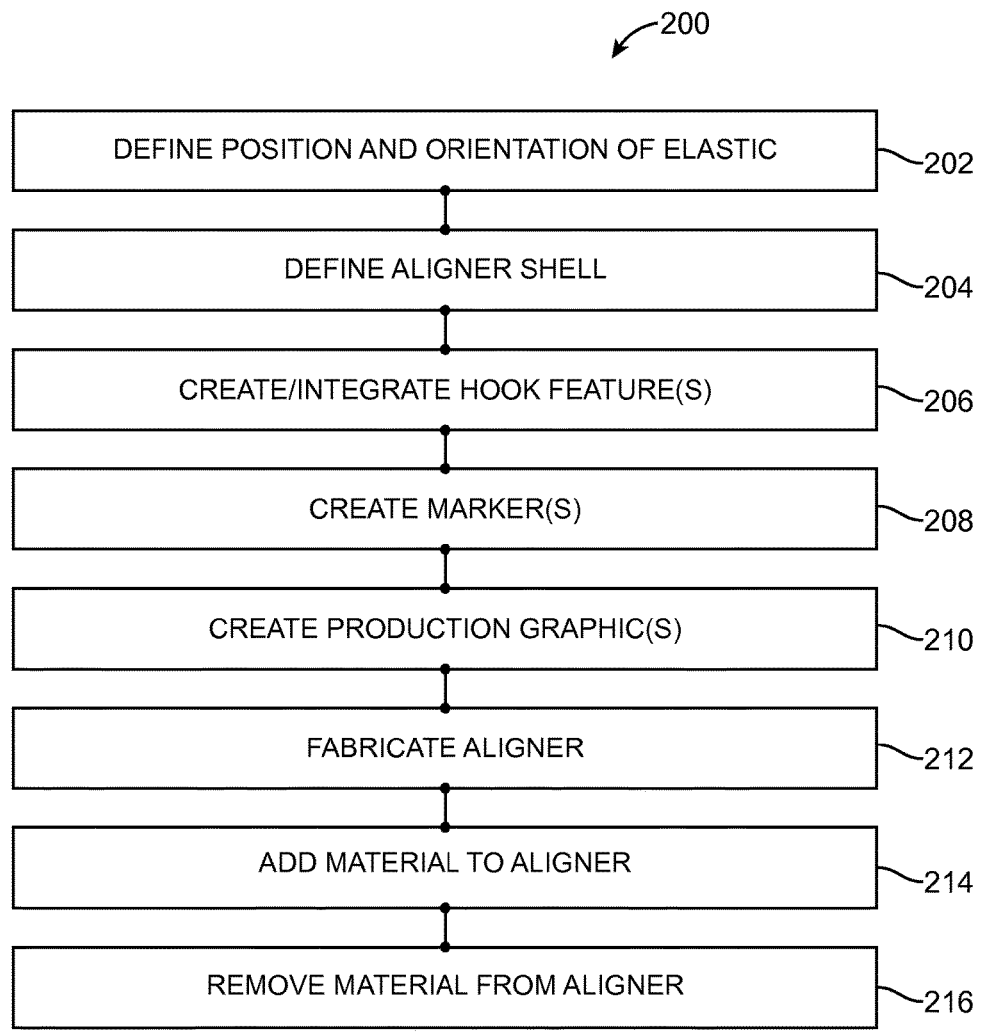
FIG. 13 is a simplified block diagram illustrating a method for direct fabrication of an aligner having an exterior hook, in accordance with an embodiment of the present invention.

FIG. 13 illustrates a method 200 for direct fabrication of an aligner having a hook, for example, via direct fabrication from a 3-dimensional representation of the aligner. Suitable direct fabrication techniques (e.g., stereo lithography) can be used. Because some of the steps of the method 200 are similar to corresponding steps of the method 100 of FIG. 11, detailed description of such steps is not repeated here. While some of the steps of method 200 are described as being computer-implemented, the alternate use of non-computer implemented approaches may also be apparent to a person of skill in the art. The method 200 can be used to generate the appliances disclosed above.

In step 202, the position and orientation of an elastic member relative to the aligner is defined. The discussion above regarding step 102 is applicable to step 202.

In step 204, an aligner shell is defined using a 3-dimensional representation of a patient's teeth. A computer program can be used to define a 3-dimensional representation of the aligner shell using representations of the patient's teeth to define the teeth receiving cavities of the aligner shell. The outer surfaces of the aligner shell can be defined, for example, using suitable offsets from the surfaces of the teeth.

In step 206, the definition of the aligner shell is modified to incorporate a hook feature, for example, one of the above disclosed hook features. To provide for efficient incorporation of such a hook feature, pre-defined digital objects can be positioned, oriented, and/or scaled relative to the aligner shell definition and then merged into the aligner shell definition. Additional material can be added and/or removed from the resulting aligner definition using known methods.

In step 208, one or more markers can optionally be created/added to the aligner definition as discussed above with respect to step 108 of the method 100. Likewise, in step 210, production graphics can be created and used as discussed above with respect to step 110 of the method 100.

In step 212, the resulting 3-dimensional representation of the aligner is used to directly fabricate the aligner. A suitable direct fabrication method, such as known rapid prototyping approaches (e.g., stereo lithography) can be used.

In step 214, material can be added to the resulting aligner as discussed above with respect to step 116 of the method 100. Likewise, in step 216, material can be removed from the resulting aligner as discussed above with respect to step 118 of the method 100.

An alternative reinforcement technique provides marked regions in the refractory model (the stereolithography model) whereby protrusions or recessed areas are designed to hold wires and/or plastic resin, which are inserted into the model, such that when the aligner sheet material is formed over the model, the reinforcements are "picked up" by the plastic formed over the reinforcements. The aligner is trimmed according to specification, leaving the reinforcement embedded into the hook region of the aligner.

Figure 14:
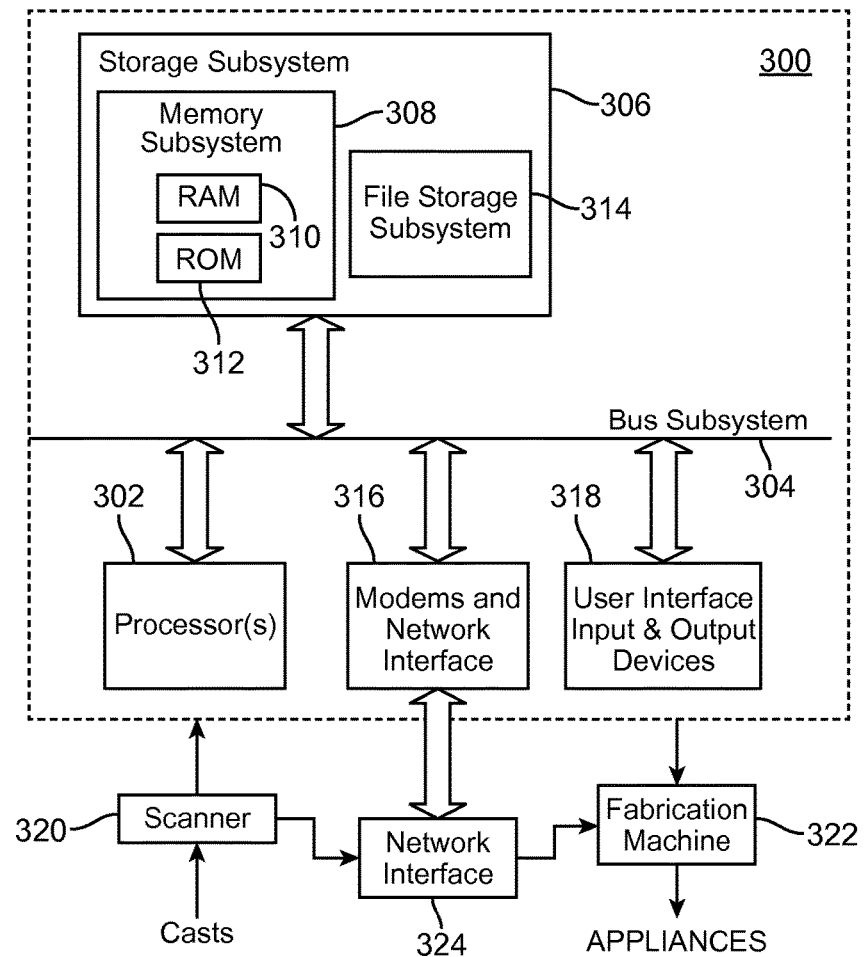
FIG. 14 diagrammatically illustrates a fabrication system in accordance with an embodiment of the present invention.

FIG. 14 is a simplified block diagram of a data processing system 300 embodying the present invention. Data processing system 300 typically includes at least one processor 302 which communicates with a number of peripheral devices via bus subsystem 304. These peripheral devices typically include a storage subsystem 306 (memory subsystem 308 and file storage subsystem 314), a set of user interface input and output devices 318, and an interface to outside networks 316, including the public switched telephone network. This interface is shown schematically as "Modems and Network Interface" block 316, and is coupled to corresponding interface devices in other data processing systems via communication network interface 324. Data processing system 300 could be a terminal or a low-end personal computer or a high-end personal computer, workstation or mainframe.

The user interface input devices typically include a keyboard and may further include a pointing device and a scanner. The pointing device may be an indirect pointing device such as a mouse, trackball, touchpad, or graphics tablet, or a direct pointing device such as a touch screen incorporated into the display. Other types of user interface input devices, such as voice recognition systems, are also possible.

User interface output devices typically include a printer and a display subsystem, which includes a display controller and a display device coupled to the controller. The display device may be a cathode ray tube (CRT), a flat-panel device such as a liquid crystal display (LCD), or a projection device. The display subsystem may also provide non-visual display such as audio output.

Storage subsystem 306 maintains the basic programming and data constructs that provide the functionality of the present invention. The software modules discussed above are typically stored in storage subsystem 306. Storage subsystem 306 typically comprises memory subsystem 308 and file storage subsystem 314.

Memory subsystem 308 typically includes a number of memories including a main random access memory (RAM) 310 for storage of instructions and data during program execution and a read only memory (ROM) 312 in which fixed instructions are stored. In the case of Macintosh-compatible personal computers the ROM would include portions of the operating system; in the case of IBM-compatible personal computers, this would include the BIOS (basic input/output system).

File storage subsystem 314 provides persistent (non-volatile) storage for program and data files, and typically includes at least one hard disk drive and at least one disk drive (with associated removable media). There may also be other devices such as a CD-ROM drive and optical drives (all with their associated removable media). Additionally, the system may include drives of the type with removable media cartridges. The removable media cartridges may, for example be hard disk cartridges, such as those marketed by Syquest and others, and flexible disk cartridges, such as those marketed by Iomega. One or more of the drives may be located at a remote location, such as in a server on a local area network or at a site on the Internet's World Wide Web.

In this context, the term "bus subsystem" is used generically so as to include any mechanism for letting the various components and subsystems communicate with each other as intended. With the exception of the input devices and the display, the other components need not be at the same physical location. Thus, for example, portions of the file storage system could be connected via various local-area or wide-area network media, including telephone lines. Similarly, the input devices and display need not be at the same location as the processor, although it is anticipated that the present invention will most often be implemented in the context of PCs and workstations.

Bus subsystem 304 is shown schematically as a single bus, but a typical system has a number of buses such as a local bus and one or more expansion buses (e.g., ADB, SCSI, ISA, EISA, MCA, NuBus, or PCI), as well as serial and parallel ports. Network connections are usually established through a device such as a network adapter on one of these expansion buses or a modem on a serial port. The client computer may be a desktop system or a portable system.

Scanner 320 is responsible for scanning casts of the patient's teeth obtained either from the patient or from an orthodontist and providing the scanned digital data set information to data processing system 300 for further processing. In a distributed environment, scanner 320 may be located at a remote location and communicate scanned digital data set information to data processing system 300 via network interface 324.

Fabrication machine 322 can encompass a range of fabrication machines and methods used to fabricate positive molds for the above-described repositioning appliances or directly fabricate the above-described repositioning appliances based on data set information received from data processing system 300. In a distributed environment, fabrication machine 322 may be located at a remote location and receive data set information from data processing system 300 via network interface 324.

It is understood that the examples and embodiments described herein are for illustrative purposes and that various modifications or changes in light thereof will be suggested to persons skilled in the art and are to be included within the spirit and purview of this application and the scope of the appended claims. Numerous different combinations or the illustrated or described embodiments are possible, including combinations of any aspects of the different described embodiments. Such combinations are considered to be part of the present invention.

What is claimed is:

1. A computer-implemented method for manufacturing an orthodontic positioning appliance having teeth receiving cavities, the method comprising:
   receiving, by a processor, a digital representation of a patient's teeth in a selected arrangement;
   modeling, by the processor, an appliance based on the received digital representation, the appliance comprising teeth receiving cavities shaped to receive and apply a resilient positioning force to the patient's teeth, the appliance comprising a hook disposed on a sidewall of the appliance and configured to interface with an orthodontic elastic member so as to react a force from the orthodontic elastic member into the appliance, the hook configured to be offset from a surface of a tooth when the appliance is coupled with the patient's teeth and no orthodontic elastic member is coupled with the hook; and
   fabricating an orthodontic appliance from the modified digital representation, wherein the hook is monolithic with a sidewall of the orthodontic appliance.

2. The method of claim 1, wherein modeling the appliance comprises modeling a reinforcement structure configured to stiffen the appliance against lateral deflection induced by the force from the orthodontic elastic member.

3. The method of claim 2, wherein modeling the reinforcement structure comprises modeling a corrugation.

4. The method of claim 2, wherein modeling the reinforcement structure comprises modeling a locally reinforced area connected with the hook to stiffen the hook against deflection induced by the force from the orthodontic elastic member.

5. The method of claim 2, wherein modeling the reinforcement structure comprises modeling a locally thickened region near the hook.

6. The method of claim 1, wherein modeling the appliance comprises:
   defining a position and an orientation of an orthodontic elastic member relative to the digital representation; and
   defining a hook edge relative to the digital representation, based on the position and the orientation of the orthodontic elastic member.

7. The method of claim 1, further comprising transmitting data representing the appliance to a fabrication system configured to fabricate the appliance.

8. A method for manufacturing an orthodontic positioning appliance having teeth receiving cavities and an external hook for an orthodontic elastic member, the method comprising:
   receiving, by a processor, a digital representation of a patient's teeth in a selected arrangement;
   defining, by the processor, a position and an orientation of an orthodontic elastic member relative to the digital representation;
   generating, by the processor, an inner surface of the external hook by modifying the digital representation of a patient's teeth to add a witness object adjacent to a tooth surface of the digital representation;
   transmitting or storing, by the processor, the modified digital representation for delivery to a fabrication system for fabricating a mold corresponding to the modified digital representation; and
   fabricating, using the mold based on the digital representation, an orthodontic appliance comprising a hook monolithic with a sidewall of the orthodontic appliance, wherein the hook is configured to interface with an orthodontic elastic member so as to react a force from the orthodontic elastic member into the orthodontic appliance.

9. The method of claim 8, wherein the hook is configured to be laterally offset from a surface of a tooth or gingivally offset from a gingival edge of the orthodontic appliance when the orthodontic appliance is coupled with the patient's teeth and absent an orthodontic elastic member coupled with the hook.

10. The method of claim 8, wherein fabricating the orthodontic appliance comprises molding a sheet of elastomeric material over the mold.

11. The method of claim 10, further comprising adding or removing material from the molded sheet.

12. The method of claim 8, wherein the witness object defines an inner surface of a portion of the hook.

13. The method of claim 8, wherein modifying the digital representation to add the witness object comprises:
   determining an area of the orthodontic appliance used to interface with the orthodontic elastic member; and
   adding the witness object to the digital representation at a location corresponding to the determined area.

14. The method of claim 8, further comprising adding one or more markers to the digital representation, the one or more markers configured to guide addition or removal of material from the orthodontic appliance.

15. The method of claim 8, further comprising modifying the digital representation to include a protrusion or a recess shaped to receive a reinforcement structure to be embedded into the orthodontic appliance.

16. A method for manufacturing an orthodontic positioning appliance having teeth receiving cavities and an external hook for an orthodontic elastic member, the method comprising:

receiving a digital representation of a patient's teeth in a selected arrangement;

defining a digital representation of an orthodontic positioning appliance;

defining a position and an orientation of an orthodontic elastic member relative to the digital representation of the orthodontic positioning appliance;

modifying the digital representation of the orthodontic positioning appliance to add a hook disposed on a sidewall of the appliance to the digital representation of the orthodontic positioning appliance; and directly fabricating an orthodontic appliance from the modified digital representation, the orthodontic appliance comprising a hook monolithic with a sidewall of the orthodontic appliance, wherein the hook is configured to interface with an orthodontic elastic member so as to react a force from the elastic member into the orthodontic appliance.

17. The method of claim 16, wherein the orthodontic appliance is fabricated using a rapid prototyping method.

18. The method of claim 16, wherein the hook representation comprises a pre-defined digital object, and modifying the digital representation to add the hook representation comprises one or more of positioning, orienting, or scaling the hook representation relative to the digital representation.

19. The method of claim 16, further comprising adding or removing material from the orthodontic appliance in order to form the hook.

20. The method of claim 16, further comprising adding one or more markers to the digital representation, the one or more markers configured to guide addition or removal of material from the orthodontic appliance.

* * * * *